(12) United States Patent
Coleman

(10) Patent No.: US 7,678,761 B2
(45) Date of Patent: Mar. 16, 2010

(54) METHOD OF PREVENTING PATHOLOGICAL LEVELS OF FACTOR VIII BEFORE, DURING AND/OR AFTER A SURGICAL PROCEDURE BY CONTROLLING PSYCHIC AND SOMATIC STRESS

(76) Inventor: Lewis S. Coleman, 560 Vista Verde Way, Bakersfield, CA (US) 93309

( * ) Notice: Subject to any disclaimer, the term of this patent is extended or adjusted under 35 U.S.C. 154(b) by 0 days.

(21) Appl. No.: 11/787,820

(22) Filed: Apr. 18, 2007

(65) Prior Publication Data

US 2007/0191430 A1    Aug. 16, 2007

Related U.S. Application Data

(62) Division of application No. 11/080,709, filed on Mar. 15, 2005.

(51) Int. Cl.
*A01N 37/18* (2006.01)
(52) U.S. Cl. .............................. 514/2; 514/12; 435/7.1
(58) Field of Classification Search ........................ None
See application file for complete search history.

(56) References Cited

OTHER PUBLICATIONS

Kehlet et al. (The Lancet, vol. 3627, pp. 1921-1928).*
Von Kanel et al. (Thromb. Haemost. 2004, vol. 92, pp. 1327-1335).*
Levine et al. (Psychosomatic Medicine, vol. 16, No. 5, pp. 398-403, 1954).*
Weiskopf et al. (J. Pharmacol Exp. Ther., Sep. 1987, vol. 242, No. 3, pp. 970-973).*

* cited by examiner

*Primary Examiner*—Hope A Robinson
(74) *Attorney, Agent, or Firm*—Cislo & Thomas, LLP

(57) ABSTRACT

A method of providing general anesthesia to an organism that improves surgical outcome by controlling a psychic and a somatic surgical stress before, during, and after a surgical procedure by preventing a pathological elevation of Factor VIII in the blood of the organism, comprising the steps of controlling the psychic stress in the organism by administering to the organism an anesthetic or hypnotic agent; controlling the somatic stress by administering to the organism an opioid and/or lidocaine; maintaining a normal body temperature of the organism; minimizing a non-surgical stress stimuli; and allowing a mild hypercarbia to support a respiratory drive in the presence of an opioid dosage. The method may further comprise the step of giving additional doses of an opioid as necessary to prevent sympathetic nervous system activation.

11 Claims, 3 Drawing Sheets

METHOD OF PREVENTING PATHOLOGICAL LEVELS OF FACTOR VIII BEFORE, DURING AND/OR AFTER A SURGICAL PROCEDURE BY CONTROLLING PSYCHIC AND SOMATIC STRESS

CROSS-REFERENCE TO RELATED APPLICATION(S)

This document is a divisional application which is copending with, and claims priority from, U.S. patent application Ser. No. 11/080,709, entitled "Therapies and Compositions for Controlling the Stress Mechanism and for Stabilizing Hemostasis in an Organism," filed Mar. 15, 2005.

TECHNICAL FIELD

The present invention technically relates to methods and compositions useful in treating surgical stress syndrome, circulatory disorders, malignancies and to methods and compositions for providing a blood substitute in an organism. More particularly, the present invention technically relates to methods and compositions that stabilize the turbulence of an organism's blood in order to treat stress-related disease.

BACKGROUND ART

The currently related art involves various diverging physiological theories. Firstly, in Stress Theory, the term "stress" is defined as follows: "1. The reaction of the animal body to forces of a deleterious nature, infections and various abnormal states that tend to disturb its normal physiologic equilibrium (homeostasis). 2. The resisting force set up in a body as a result of an externally applied force."

Secondly, in Disorder Theory, the term disorder is involved in the basic law of the universe. Living creatures are ordered forms that employ combinations of information systems, chemical reactions, and mechanical mechanisms to acquire energy from their environment in order to maintain their structural integrity and function as well as to replicate. To be alive is to be unceasingly stressed by the demands of energy acquisition and structural maintenance.

Thirdly, Occam's Razor, a key theory or concept in scientific philosophy, suggests that the best approach to a complex problem is to assume that the simplest explanation, or set of explanations, is correct until proven otherwise.

That humans and animals are equipped with physiological mechanisms that enable them to resist and repair the damaging effects of stressful stimulus, including coagulation, inflammation, scab formation, wound repair, and tissue maintenance, has been long understood. The observed reactions to stress are numerous, confusing, and interrelated; and thusfar, no attempt has been made to describe a single mechanism in the related art that can explain these various phenomena.

The Stress Theory may provide fresh insights to the nature of embryology, neonatology, physiology, immunology, pharmacology, and pathology. The Stress Theory may offer improved understanding of the mechanisms of drug actions, systemic vascular resistance, blood flow and distribution, blood pressure, atherosclerosis, thromboembolism, capillary homeostasis, apoptosis, embryological tissue development, muscle hypertrophy, athletic cardiovascular "conditioning", blood coagulation, tissue inflammation, wound healing, Virchow's Triad, the "Fight or Flight" stress syndrome of Hans Seyle, Surgical stress, tissue remodeling and maintenance, as well as numerous manifestations of pathology by describing all these in terms of the effects of a cohesive stress-opposing mechanism that operates continuously to maintain homeostasis and tissue integrity in the animal body.

Stress Theory is predicated on the alternate hypothesis that coagulation Factors VII and VIII are blood-borne stress agents that respectively cause local and systemic elevations of thrombin levels and synergize each other's actions to produce hyper-elevations of thrombin at the site of stress (injury) and that thrombin is responsible for the numerous symptoms and effects exerted by the stress mechanism. Stress Theory offers a simpler and more complete explanation of hemostasis and coagulation than presently prevailing Cascade Theory, plus a simple explanation of wound healing, tissue maintenance, and important aspects of embryological development that is presently lacking.

Stress Theory assigns a role to Factor VII that might be compared to the "Extrinsic" cascade. Factor VII circulates in flowing blood and is separated from exposure to the underlying collagen that constitutes the major component of blood vessel structure by the vascular endothelium, which is only one-cell-layer in thickness. Disruption of the vascular endothelium, therefore, exposes Factor VII to collagen, thereby causing its activation, which is normally localized and focused the effects of the Stress Mechanism at the site of injury (stress).

Likewise, the role of Factor VIII loosely corresponds to the "Intrinsic" cascade. Factor VIII is a hormone that is produced and is released directly into the blood by the vascular endothelium, a gland, under the control of the Sympathetic Nervous System (SNS), so that its level varies with the tone and activity levels of the SNS. Factor VIII's activity is systemic and its function is to regulate the activity level of the Stress Mechanism.

Both Factors VII and Factor VIII activate thrombin, and their combined effects cause localized hyper-elevations of thrombin that focus the effects of the stress mechanism at the site of stress and injury. The role of thrombin, thus, corresponds to the "Final Common Pathway" as described by Cascade Theory.

Stress Theory hypothesizes that thrombin is the primary enzymatic effecter agent of the stress mechanism. Thrombin is the known cause of numerous effects, including platelet activation, cell mitosis, cell hypertrophy, increased cell metabolism, inflammation, collagen production, and the conversion of fibrinogen to insoluble fibrin. Thrombin is closely associated with embryological development, wound healing, coagulation, malignancy, and tissue maintenance. Stress Theory hypothesizes that thrombin produces these multiple effects via a common mechanism that has yet to be identified in the related art.

Stress Theory postulates two mechanisms of hemostasis, both of which are controlled by blood levels of thrombin and "insoluble" fibrin. These mechanisms are: 1) Capillary Hemostasis, which is initiated by closure of a molecular level Capillary Gate Mechanism governed by varying levels of "insoluble" fibrin and 2) Systemic Hemostasis, which is manifested by the familiar blood clot formation process that occurs in larger vessels. Hemostasis is initiated by declines in blood turbulence and mixing, which, in turn, is initiated by increased blood levels of "insoluble" fibrin, a three-dimensional molecule with physical properties absent in its precursor, "soft" fibrin, and is enhanced by the formation of fibrin strands that connect various blood components to one another as turbulence and mixing decline.

The Stress Theory implies that changes in systemic vascular resistance occur in accord with the operation of the Capillary Gate Mechanism and the degree of capillary hemostasis as opposed to muscular contraction or relaxation of larger blood vessels. The Stress Theory asserts that the rapidly reversible physical properties of the three-dimensional matrix structure of insoluble fibrin, as controlled and facilitated by varying levels of Factor VIII, enable the opening and closing of the hypothesized Capillary Gate Mechanism to produce capillary hemostasis and indirectly regulate capillary perfusion. Simultaneously, insoluble fibrin increases systemic blood viscosity, which reduces blood turbulence and mixing, thereby increasing blood coagulability and thereby inducing clot formation. Hyper-elevations of insoluble fibrin in the immediate vicinity of stressful stimulus (injury), determined by the combined effects of Factors VII and VIII, reduce turbulence and mixing below a critical threshold, whereupon fibrin strands form inter-connections among blood components that further reduce turbulence and mixing, and clot formation proceeds to completion.

Chronic systemic elevations in blood viscosity, caused by persistent stressful stimulus and other factors, in turn, cause reductions in blood turbulence and mixing that accelerate atherosclerosis in the arterial tree and increase the risk of thromboembolism in the venous system. Systemic vascular resistance and blood pressure vary directly and cardiac output and tissue perfusion vary inversely, with the degree of closure of the Capillary Gate Mechanism as determined by the level of stress, SNS activation, and Factor VIII release.

Although thrombin plays an essential role in coagulation, most thrombin generation occurs after clot formation, suggesting that it may have additional functions. Stress Theory postulates that thrombin initiates coagulation and inflammation as a prelude to wound healing as well as attracts various wound-healing cell types to the site of injury. Thrombin subsequently induces fibroblast mitosis, metabolism, proliferation, and collagen production as an integral part of the wound healing process. Thrombin levels continue to be elevated at the site of stress to regulate the wound-healing process in accord with continued collagen exposure to flowing blood. Thereby maintaining Factor VII activation when wound healing is substantially complete and collagen is sealed from exposure to flowing blood, thrombin levels fall. The decline in thrombin levels induces fibroblast apoptosis, thereby signaling an end to the "active phase" of wound healing. Maintenance levels of thrombin may stimulate collagen replenishment and tissue maintenance and remodeling, as evidenced by skin necrosis, ulceration, and disturbances of wound repair that sometimes result from treatment with coumadin, wherein coumadin exerts anti-thrombin effects.

Growing evidence suggests that the embryological development of complex multi-celled eukaryotic organisms may be largely governed by genetic programming contained in "junk" DNA in the form of "introns" that, in the case of humans, constitutes 95 percent or more of the genome. The introns may exert their effects on embryological development by controlling the timing of developmental processes, such as stem cell maintenance, cell proliferation, and apoptosis. Thrombin has been shown to be closely associated with cell maintenance, metabolism, hypertrophy, proliferation, angiogenesis and apoptosis. Thrombin appears to play an important role in embryological development, as evidenced by fetal developmental defects that are associated with the administration of thrombin inhibitors to pregnant females and studies that demonstrate the role of thrombin in embryological development. Thus, the present hypothesis considers that introns control embryological development by controlling localized thrombin levels at precise time intervals. The Stress Mechanism, which also governs thrombin levels, may play a complimentary and synergistic role in embryological development by stimulating newly-developed organs and tissues to grow and enlarge in response to the stresses associated with fetal development. Assuming the presence of thrombin-sensitive growth and mitosis receptors common to all cells, the combined effects of introns and the stress mechanism to regulate thrombin levels may provide a simplified model of embryological development in complex organisms.

Nearly all forms of disease cause activation of the Stress Mechanism, typically manifested by a triad of factors: (1) elevated blood levels of Factor VIII, (2) increased blood viscosity, and (3) increased blood coagulability. These factors are often accompanied by a wide variety of seemingly unrelated pathological symptoms due to inflammation, fibrin generation, and fibroblast proliferation. The Stress Mechanism may account for these symptoms. The Stress Mechanism is powerful, and may cause pathological effects, including malignancy, that are at odds with its healing function. The cause of these symptoms has not yet been fully understood in the related art. As such, stress-related diseases, such as rheumatoid disease, the tissue damage of diabetes, ARDS, asthma, inflammatory bowel disease, malignancy, eclampsia, and DIC remain misunderstood. As such, the condition in relation to the manner in which stress-related conditions appears to exacerbate the incidence and severity of one another, e.g. in diabetes, pregnancy, or CREST syndrome also remains misunderstood the related art, the fact that patients afflicted with one form of cancer are at increased risk of additional forms of cancer, the manner in which conditions that activate the stress mechanism may increase the risk of atherosclerosis and malignancy and the manner in which environmental factors may increase the risk of stress-related disease also remain problematic in the related art. The associations between hypertension, systemic vascular resistance, blood viscosity, blood coagulability, atherosclerosis, and heart disease remain a mystery in the related art, whereby new forms of treatment and research are stymied. Finally, logical ways to employ anesthesia and surgical techniques to control stress and improve surgical outcome have yet to be seen in the related art.

The Stress Theory is based on a set of inter-related, testable hypotheses, related to further factors.

A Stress Mechanism is present in all vertebrate species that involves the activities of Factors VII, Factor VIII, and thrombin. The Stress Mechanism operates continuously to control coagulation, scab formation, wound healing, and tissue maintenance. "Stress" is defined as any stimulus that causes activation of the Stress Mechanism.

A sub-microscopic, molecular-level Capillary Gate Mechanism exists that is controlled by the effects of Factors VII and VIII and is an integral component of the Stress Mechanism. The Capillary Gate Mechanism regulates capillary hemostasis. The degree of capillary hemostasis, i.e., closure of the Capillary Gate Mechanism, indirectly affects capillary bed perfusion, systemic vascular resistance, blood pressure, and cardiac output.

Factor VIII is a systemic stress hormone that is continuously released into the bloodstream by a gland called the vascular endothelium which is under the direct control of the Sympathetic Nervous System (SNS) in accordance with constantly varying levels of stressful stimulus. The function of Factor VIII is to control the activity level of the Stress Mechanism. Factor VIII comprises the following components: Factor VIIIC and Von Willebrand's Factor (VWF). The VIIIC component causes the systemic conversion of prothrombin to thrombin and the activation of Factor XIII, whereby fibronectin cross-links are added to developing fibrin strands to form a three-dimensional "insoluble" fibrin molecule. The VWF component stabilizes, enhances, and prolongs the function of the VIIIC component, thereby indirectly affecting thrombin activity. The VWF molecule also serves as a molecular component of the Capillary Gate Mechanism.

Factor VII is a companion stress agent that is activated by exposure to collagen. The actions of Factor VII occur at the site of tissue disruption. Like Factor VIII, Factor VII catalyzes the conversion of prothrombin to thrombin and thereby synergizing the effects of Factor VIII to produce localized hyper-elevations of thrombin, and thereby focusing the effects of the Stress Mechanism on the site of stress (injury).

Elevated blood levels of thrombin cause elevated blood levels of insoluble fibrin. Insoluble fibrin simultaneously causes both closure of the Capillary Gate Mechanism and elevations in blood viscosity. Increased blood viscosity causes "damping" (decrease) in blood turbulence and mixing. Thrombin also stimulates the activation of fibroblasts and other cell types to control embryonic organ development, wound healing, and tissue maintenance.

Turbulence and mixing induced by pulsatile blood flow, inhibits both atherosclerosis and coagulation. Coagulation occurs spontaneously when turbulence and mixing fall below a critical threshold. Atherosclerosis is accelerated by chronically lowered levels of turbulence and mixing in the blood.

Under ordinary circumstances, coagulation occurs only in the presence of the combined effects of Factors VII and VIII. The combined effects are synergized so as to induce hyper-elevations of thrombin at the site of injury that lowers turbulence and mixing below the threshold of clot formation.

The VIIIC component of Factor VIII is so unstable that it is completely inactive in the absence of VWF. Variations in the quality and/or quantity of VWF, therefore, cause variations in both the half-life and activity levels of Factor VIII. This circumstance explains the various coagulation-enhancing effects of VWF and the manner in which increased levels of stress cause the half-life of Factor VIII to be prolonged, regardless of subsequent lowering of SNS activity levels.

The other effects of thrombin, including inflammation, cell proliferation, collagen production, and increased cell metabolism, are regulated by the Stress Mechanism in the same manner as coagulation so as to govern the wound-healing process, key aspects of embryological development, and tissue remodeling and maintenance.

Factor VIII is released in response to pure psychic stress, thereby causing pre-emptive elevations in blood coagulability and capillary hemostasis and thereby minimizing blood loss in the event of subsequent injury. Further, Factor VIII functions as an integral part of the "fight or flight" stress phenomenon described by Hans Selye.

The hitherto mysterious pathological effects associated with Surgical Stress and the Stress Syndrome, including dementia, stroke, myocardial infarction, bowel ileus, vasomotor instability, and sudden death, are primarily explained by widespread and prolonged stress-induced closure of the Capillary Gate Mechanism that results in tissue oxygen starvation and damage in affected capillary beds. This will be called "Capillary Fibrin Stress" (CFS). Microvascular disturbances in nervous tissue may offer an example of CFS.

Apoptosis is caused by a sudden decline of thrombin levels below a critical threshold required to sustain fibroblast metabolism and mitosis. This circumstance normally signifies the completion of the active phase of wound healing and plays a critical role in embryological development.

Malignancy is an aberration of the wound-healing process in which prolonged and excessive levels of stressful stimulus and hyper-elevated thrombin levels cause the invasion of normal tissues by thrombin-activated fibroblasts; thereby resulting in a self-sustaining release of thrombin that inhibits apoptosis.

SNS activity levels are stimulated by semi-independent pathways for psychic stress, i.e., conscious awareness of pain and danger, and somatic stress, i.e., physical tissue disruption. The simultaneous control of both psychic and somatic stress is necessary to produce synergistic reductions in SNS and Stress Mechanism activity levels that may prevent CFS, systemic inflammation, hypercoagulability, and other pathological effects of stressful stimuli and Surgical Stress.

The various elements of the Stress Theory will be discussed in detail. Clinical examples, including eclampsia, essential hypertension, diabetes, DIC, and ARDS will be offered as illustrations of the role that stress may play in disease. FIG. 1 (related art) shows a diagram providing an outline of the proposed Stress Mechanism.

Recent advances in the understanding of the characteristics of Factor VIII may offer fresh insight as to the presence and nature of a fast-acting, sub-microscopic, molecular-level Capillary Gate Mechanism. A mechanism that regulates blood flow and hemostasis at the capillary level has long been suspected, but never identified. The Capillary Gate Mechanism hypothesis is attractive because it offers an explanation of observed capillary hemostasis. Capillaries lack musculature and cannot contract, so capillary vasoconstriction is impossible. However, capillaries and vascular endothelium have been shown to be innervated with both sympathetic and parasympathetic nerve endings that may govern the release of Factor VIII and other vasoactive substances. Theories of capillary endothelial cell swelling that occlude the capillary lumen have been proposed in the related art, but are not supported by any evidence. Theories of pre-capillary sphincter contraction that might explain capillary hemostasis are likewise lacking in substance, because pre-capillary sphincters and vessels invariably relax after short periods of contraction and subsequently exhibit compensatory vasodilation.

The Capillary Gate Mechanism hypothesis also offers an improved explanation for the regulation of blood flow as well as distribution and systemic vascular resistance. The surface area of the capillaries is many times greater than that of all larger vessels combined; and the hemodynamic pressures and flows are vastly lower so that control of blood flow might be more easily explained at the capillary level than at the level of larger blood vessels. The Capillary Gate Mechanism hypothesis might also offer an improved explanation of the Blood Brain barrier and cerebral autoregulation.

Witte et al. have demonstrated microvascular endothelial receptor sites for fibrinogen, fibronectin, and Factor VIII, suggesting that these are structural elements of the Capillary Gate Mechanism. Since insoluble fibrin contains fibronectin, the present invention considers that fibronectin receptor sites may actually serve as attachment sites for insoluble fibrin. The invention considers that the Capillary Gate Mechanism is regulated by the blood level of Factor VIII, as determined by the activity level of the Sympathetic Nervous System. Rising levels of Factor VIII cause increased blood levels of thrombin, which cause elevated levels of insoluble fibrin, whereupon both Factor VIII and insoluble fibrin act in concert with fibrinogen to obstruct capillary flow and close the Capillary Gate.

Thrombin has been demonstrated to inhibit the conversion of plasminogen to plasmin, and insoluble fibrin contains plasminogen that is an integral part of its structure. The present invention considers that when levels of Factor VIII decline, the resulting decrease in thrombin level allows spontaneous conversion of plasminogen to plasmin, which attacks and dismembers the insoluble fibrin molecule into "fibrin split products." In addition, enzymes such as urokinase and Tissue Plasminogen Activator (TPa) may attack insoluble fibrin and prevent closure of the capillary gate in certain tissues where uninterrupted capillary perfusion is vital, such as brain and heart tissue. This circumstance might explain the "blood/brain barrier" and cerebral autoregulation.

In addition, the observations of Holemans et al. that vasoactive drugs are associated with elevated rates of fibrin turnover and that "vasodilators" are associated with greater levels of fibrin turnover than "vasopressors" is consistent with the foregoing concept. The present invention considers that vasopressors enhance fibrin formation and the closure of the Capillary Gate, while vasodilators enhance the breakdown of fibrin and the opening of the Capillary Gate. These agents may effect changes in systemic vascular resistance and, therefore, blood pressure by manipulating the operation of the Capillary Gate.

Angiodysplasia, an age-related bleeding diathesis in which visible damage to capillaries occurs, may offer direct evidence of a Capillary Gate Mechanism. Angiodysplasia has been shown in all studied forms to be associated with damaged or absent VWF, and it occurs in von Willebrand's Disease. Angiodysplasia also occurs in uremia, aortic stenosis, and Idiopathic Hypertrophic Subaortic Stenosis, all of which have been shown to be associated with functional abnormalities of the VWF molecule. In the absence of adequate levels of functioning VWF, the half-life of the VIIIC component of the Factor VIII complex becomes undetectable. As such, severe defects in the quality or quantity of VWF results in complete cessation of all aspects of Factor VIII complex activity. In contrast, angiodysplasia does not occur in classical hemophilia, wherein only VIIIC is absent and normal levels of VWF are present. This circumstance suggests that the VWF portion of the Factor VIII complex plays a dominant role in Capillary Gate function compared to the VIIIC component, and it defects in the quality or quantity of VWF which causes a structural defect in the Capillary Gate Mechanism so severe as to result in visible capillary damage known as angiodysplasia.

Fibrin "cuffs" and deposits have been noted at the entrance and in the lumen of capillaries in association with venous obstruction. Fibrin deposits in blood vessels and tissues and hyper-elevations of blood coagulability are consistently observed in association with severe stress states. These observations are consistent with hyper-elevations of blood fibrin levels that commonly occur in states of stress. The present invention considers the hypothesis that severe stress may cause overproduction of insoluble fibrin that normally functions to close the Capillary Gate Mechanism and regulate blood coagulability, with the result that excess fibrin accumulates at the entrance of the capillary gate and deposits on vessel walls, as in DIC.

Sielenkamper et al. have demonstrated the existence of unexplained increases in bowel capillary flow in association with epidural anesthesia, despite lowered systemic blood pressure. Kabon et al. have demonstrated increased tissue oxygenation associated with epidural anesthesia, again despite lowered systemic blood pressure. Kapral et al. have demonstrated higher pH in bowel tissue associated with epidural anesthesia. Epidural anesthesia has been associated with reduced thrombophlebitis, reduced blood loss, increased stroke volume, decreased systemic vascular resistance, and overall decrease in morbidity as well as mortality in high risk patients. These studies are consistent with the hypothesis that epidural anesthesia may interfere with the systemic release of Factor VIII by decreasing SNS tone and activity levels, thereby reducing blood levels of insoluble fibrin, thereby preventing closure of the Capillary Gate, and thereby improving capillary bed perfusion.

Sielenkamper et al. have also demonstrated unexplained decreases in bowel capillary flow in association with sepsis, a powerful cause of stress. Sepsis is known to cause stressful effects and elevations in blood levels of Factor VIII. The observed decreases in capillary flow may be explained by closure of the Capillary Gate caused by sepsis-induced elevated levels of Factor VIII.

Luostarinen et al. demonstrated unexplained injury-induced decreases in adjacent (uninjured) bowel capillary flow that was restored by direct application of lidocaine. The decreases in capillary flow may be explained by the activities of Factors VII and VIII in the vicinity of injury. The present invention considers that the direct application of lidocaine to capillary beds may block the function of exposed SNS nerve endings that terminate in the capillary endothelium, thereby preventing the release of Factor VIII, and thereby opening the Capillary Gate and restoring of capillary flow.

Weinberg et al. have demonstrated that bupivacaine inhibits the accumulation of acidic products of anaerobic glycolysis during ventricular fibrillation (VF) in dogs, whereas tissue oxygen levels are not affected. However, Weinberg et al. could not explain this result. Like lidocaine, intravenous dosage with bupivacaine may interrupt the function of exposed nerve endings in the vascular endothelium, thereby inhibiting the release of Factor VIII and preventing the closure of the Capillary Gate Mechanism. This condition might promote capillary perfusion or diffusion during VF, thereby mitigating the accumulation of acidic metabolic products in cardiac tissue during VF. Oxygen levels would be expected to be depleted rapidly regardless of the effects of bupivacaine, VF would interrupt the transport of oxygen via systemic circulation. Thereby causing cardiac tissue to rapidly deplete oxygen stores and revert to anaerobic glycosis metabolism, which, in turn exacerbates the production of acidic metabolic products.

Anaphylactic shock may also provide insights to Capillary Gate structure and function. Anaphylactic shock differs from other forms of shock in that it is not associated with elevated fibrin levels or decreased cardiac output, but is characterized by severe hypotension, hives, and angioneurotic edema that may cause swelling of airway tissues so severe as to result in death. Anaphylactic shock is associated with repeated exposure to antigenic drugs and chemicals, notably protamine and bee venom, but can be successfully treated with epinephrine, which a compound causes the release of Factor VIII and enhances the conversion of fibrinogen to insoluble fibrin. The present invention considers that the cause of anaphylaxis symptoms may be a sudden, widespread failure of the Capillary Gate Mechanism that causes a severe translocation of red cells and plasma from large blood vessels to capillaries and extravascular space. Such a phenomenon might occur if the immune system were to attack one of the Capillary Gate components in association with exposure to antigen, thereby causing sudden, widespread failure of the Capillary Gate mechanism. Existing studies suggest that anaphylaxis may involve sudden a complement-mediated attack on the VWF molecule followed by activation of plasminogen, thereby causing widespread destruction of the insoluble fibrin molecule as thrombin levels fall in response to the inactivation of VWF. These studies are consistent with the hypothesis that insoluble fibrin and VWF are important structural components of an existing Capillary Gate Mechanism. FIG. 2 (related art) shows a diagram of the mechanism of the Capillary Gate.

Serine protease thrombin is a powerful, multifunctional and ubiquitous stress enzyme that plays a central role in coagulation, DIC, injury, inflammation, blood vessel repair, and tissue remodeling.

Thrombin mediates embryological cell proliferation and tissue development, as evidenced by serious birth defects that occur with fetal exposure to anti-thrombin medications, and it inhibits apoptosis. Declines in thrombin levels may, therefore, explain the apoptosis that plays an important role in both embryological development and wound healing.

Thrombin is routinely employed in the operating theatre to control bleeding from cut surfaces because it mediates platelet activation and fibrin deposition. Thrombin also stimulates fibroblast metabolism, proliferation, hypertrophy, and collagen production as an integral part of wound healing. However, Thrombin supports and promotes malignancy. Thrombin may activate leukocytes, polymorphonucleocytes, monocytes, macrophages and endothelial cells as part of the inflammatory process and stimulates angiogenesis. Thrombin has been associated with abnormal proliferation of vascular smooth muscle cells and pathogenic vascular remodeling. Chronic hypoxia, chemical exposure, and other forms of stress, may induce thrombin-mediated pathological forms of tissue proliferation. Thrombin may mediate cellular hypertrophy and tissue hypertrophy such as muscular hypertrophy, that occur with mechanical stress to muscles. Thrombin's mitogenic effects appear to be inhibited by glucocorticoids. Thereby explaining certain therapeutic effects of these agents.

Thrombin generation appears to depend on the presence of calcium and Factors VIII and IX. During the coagulation process, thrombin enzymatically cleaves fibrinogen into fibrin "monomers" that polymerize into strands ("soft" fibrin). Thrombin simultaneously catalyzes the activation of Factor XIII ("fibrin stabilizing factor"), which forms fibronectin cross-links in the developing fibrin structure so as to produce a three-dimensional fibrin "matrix" structure known as "insoluble" fibrin. Thrombin directly induces platelet activation and platelet elaboration of thromboxane, thereby causing vasoconstriction and reduced blood flow in the immediate vicinity of activated platelets.

Thus, a long-felt need is seen to exist for a unified theory that endeavors to explain the biological reaction to stressful stimuli in terms of a simple, physiologic mechanism. Furthermore, a long-felt need is seen to exist for therapies and compositions which utilize unified principles of stress, coagulation, inflammation, wound healing, embryological development, and tissue maintenance.

DISCLOSURE OF THE INVENTION

The present invention addresses the problems in the related art and involves the clinical benefits of opioid-based anesthetic strategies as well as a stress monitor.

The present invention takes into consideration that thrombin stabilizes the plasminogen which is incorporated into the fibrin matrix and prevents the plasminogen from spontaneously converting to plasmin, thereby preventing plasmin from attacking the fibrin matrix and subsequently reducing it to "fibrin split products." Elevated levels of thrombin, thus, preserve the integrity of the "insoluble" fibrin structure which appears to spontaneously disintegrate when levels of Factor VIIIC and thrombin decline. As such, Factor VIIIC is believed to control the Capillary Gate Mechanism by regulating thrombin levels.

The present invention takes into consideration that these seemingly disparate effects of thrombin are mediated via a common mechanism that is presently obscure in the related art. The present invention recognizes that thrombin is the primary effecter enzyme of the Stress Mechanism. Thrombin is activated by both Factor VII as well as the VIIIC component of Factor VIII complex and appears to control both coagulation and wound healing.

Often, the effects attributed to thrombin have also been attributed to other enzymes. For example, direct platelet activation has been attributed to Factor VIII, collagen, Factor VII, other platelets, as well as thrombin. The present invention is premised on the assumption that, in the absence of evidence to the contrary, any effects attributed to a combination of thrombin and another factor are directly caused by thrombin, unless proven otherwise, and that the other factors operate indirectly by activating thrombin.

In discussing the roles of fibrin, fibrinogen, and fibronectin in the present invention, a "dynamic equilibrium" in the blood between the processes of coagulation and anti-coagulation is understood, but the exact nature of this equilibrium has never been previously described in the related art. In the present invention, a model of the processes comprises a homeostatic equilibrium existing between fibrinogen and fibrin that is governed by the opposing effects of Factor VIII and plasminogen. Factor VIII acts via thrombin to convert fibrinogen to fibrin and to cause elevations in blood levels of insoluble fibrin, but plasminogen rapidly converts to plasmin when blood levels of Factor VIII decline. Subsequently, the plasmin attacks and dismantles the "insoluble" fibrin matrix. The dismantling process typically causes elevations in "Fibrin Split Products" or d-Dimers which appear to be remnants of insoluble fibrin and are associated with increased risk of cardiovascular disease. In addition to this basic mechanism of fibrin formation and spontaneous self-destruction, independent mechanisms governing fibrinolysis are believed to exist that involve urokinase, tissue plasminogen activator (TPA), and activated Protein C. These mechanisms may serve to prevent the closure of the Capillary Gate Mechanism under various circumstances.

Thrombin causes the conversion of fibrinogen to "insoluble" fibrin. Insoluble fibrin is a three-dimensional structure that appears to incorporate fibronectin, a glycoprotein present in the blood. The conversion of fibrinogen to insoluble fibrin requires at least approximately five minutes in a test tube, but the conversion is believed to occur more rapidly in vivo. According to researchers, Ellison and Jobes, in the related art, "Native fibrinogen (molecular weight 343,000 daltons) is composed of three pairs of non-identical peptide chains (Aa2, Bb2, Gamma2) stabilized by disulfide bonds. These are the fibrin monomers. To accomplish the conversion of fibrinogen to fibrin, thrombin catalyzes the cleavage of fibrinopeptides A and B from the Aa and Bb chains, yielding the a and b chains of the fibrin monomer, which polymerize into lengthening strands to yield a soluble form of fibrin. Thrombin then catalyzes the activation of the fibrin-stabilizing factor (Factor XIII), which catalyzes the formation of intermolecular cross-links between the gamma chains (forming gamma-gamma dimers), and between the a-chains (forming a-a multimers)."

However, in the present invention, fibronectin may be incorporated into this three-dimensional cross-link structure to form a "matrix" structure. That coagulopathy is related to defects in the quality or quantity of Factor XIII illustrates the importance of affecting the cross-linked, three-dimensional form of insoluble fibrin. The present invention comprises an insoluble fibrin, a very large three-dimensional molecular structure, which possesses unique physical properties that enable it to simultaneously induce closure of the Capillary Gate Mechanism and increase blood viscosity, thereby decreasing turbulence and mixing, and thereby increases blood coagulability so as to control the coagulation process.

So-called "soft" fibrin, comprising fibrin strands without cross-links, is present in the condition of classical hemophilia, wherein the VIIIC component of the Factor VIII complex is absent, and wherein insoluble fibrin is not produced in appreciable amounts due to the resulting defect in thrombin production and Factor XIII activation. As such, the critical defect in hemophilia is believed to be the inability to convert "soft" fibrin to insoluble fibrin in functional quantities. The resulting inability to regulate blood coagulability and capillary hemostasis may explain the bleeding diathesis that occurs in both hemophilia and in von Willebrand's Disease.

Fibronectin is a glycoprotein (disulfite-bonded dimer of 200-220 Kd subunits) that appears to be secreted by the vascular endothelium into blood. Fibronectin is also found in an insoluble fibrillar form as a component of connective tissue matrix, such as collagen (proteoglycans) and other forms molecular complexes comprising collagen, fibrinogen, fibrin, heparin, activated factor XIII, and bacteria, to form "domains" or subunits which mediate adhesion of cells to other cells or cells to biomaterials, cells to tissue, or mediate cell migration, chemotactic activity, and tissue stromal organization. Fibronectin also interacts with hemostatic and fibrinolytic systems and is a part of the fibrinous blood clot. Also, fibronectin plays an important role in wound healing and in the formation of immune complexes. Depletion of fibronectin due to hyper-activation of the Stress Mechanism in sepsis may worsen the outcome; and fibronectin replacement is believed to be an effective treatment. In eclampsia, increased circulating levels of fibronectin and Factor VIII are associated with glomerular endotheliosis and hypertension.

Calcium, and possibly an external source of energy, may be essential for the conversion of soluble fibrin to insoluble fibrin matrix. Calcium appears to be elevated in association with thrombin activity; and elevated calcium is also associated with the inhibition of plasmin action. Sodium citrate inhibits clot formation by absorbing calcium. The addition of calcium to citrated blood restores the clotting process. Calcium is used to achieve therapeutic hemostasis; and sodium citrate is used to control coagulation in hemodialysis.

Plasmins dissolve fibrin, yet small quantities of plasminogen (the plasmin precursor) are adsorbed onto fibrin at lysine-binding sites, thereby becoming an integral part of the insoluble fibrin matrix. Since both plasminogen and plasminogen activators are incorporated into the fibrin matrix, the presence of a mechanism for causing a rapid dissolution or "self destruction" of the fibrin matrix is believed to be inhibited. If the situation is otherwise, the fibrin structure would be inherently unstable. As noted previously, thrombin is believed to inhibit plasminogen.

Regarding amyloidosis, a direct relationship between fibrin split products (FSP) and amyloid protein is believed to exist. Like FSP, amyloidosis is associated with excessive fibrin "turnover" in the presence of elevated levels of urokinase; and amyloidosis is associated with atherosclerosis. Amyloid protein appears to interfere with coagulation by competing with fibrin precursors, particularly Factor X, suggesting a structural similarity between FSP and amyloid protein. Like fibrin, amyloid protein appears in the form of chains or fibrils. Fibronectin, a component of insoluble fibrin, and vitronectin, a component of amyloid; are both glycoproteins, and may be closely related. Both fibrin breakdown products and amyloid appear to be associated with hypercoagulability states; and they both interfere with coagulation. As such, they are believed to be directly related. Like fibrin, amyloid protein tends to appear as deposits in vessels and organ tissues in association with stressful conditions; and this scenario may be a largely unappreciated source of pathology in the related art. Occult amyloid deposits that damage blood vessels and surrounding tissues may be a factor in congestive heart failure and ischemic colitis. Amyloid protein appears in rheumatoid nodules, the synovium, and other tissues of patients afflicted with rheumatoid arthritis as well as other rheumatoid diseases. Amyloid protein may be a cause or a contributing factor in the development of diabetes, a stress-related condition, and Alzheimer's Disease.

In the present invention, amyloid protein is believed to be in a form of "fibrin split products" or d-dimer that has undergone a conformational change that renders it distinct. Amyloid protein and fibrin degradation products may represent the "exhaust" produced by the operation of the Capillary Gate Mechanism, and increased levels of these proteins in the blood may be caused by opening and closing of the Capillary Gate Mechanism by urokinase, vasoactive drugs, or stress-related factors. The present invention takes into consideration that rheumatoid diseases represent clinical manifestations of amyloidosis.

With respect to Factor VIII, the "classical" hormonal response to trauma is described as activation of the hypothalamic-pituitary-adrenal axis and the SNS, both interacting with immunological responses. Neither Factor VIII nor Factor VII has been previously associated with this concept in the related art, but their proposed roles in the Stress Theory may offer an improved explanation of the effects of stress. In particular, the present invention considers that Factor VIII is a stress hormone being secreted directly into systemic circulation under SNS control by the vascular endothelium, a gland. Factor VIII is released into the blood circulation under circumstances similar to those in which other stress hormones, such as epinephrine, glucagon, and cortisol are released. Factor VIII's function is to regulate the activity level of the Stress Mechanism, including systemic blood coagulability and Capillary Gate closure, to synergize its effects with the localized effects of Factor VII, a companion stress enzyme, and to further induce localized hyper-elevations of thrombin that initiate coagulation and regulate wound healing at the site of injury or stress. Factor VIII may be elevated in response to either psychic or somatic pain and stress, or both, as well as other forms of stressful stimuli that increase SNS activity levels. Factor VIII may thus be purposefully and preemptively released, i.e., prior to actual injury so as to minimize blood loss, in accordance with the present invention, well beyond that of the mere "fight or flight" stress mechanism described by Hans Selye in the related art.

Factor VIII comprises two very large molecules, i.e., VIIIC and VWF. These molecules circulate together in the blood and synergistically exert their effects. Unlike other known coagulation proteins that are produced in abundance by the liver and that have prolonged, stable half-lives, Factor VIII is produced in the vascular endothelium and normally has a brief half-life of some 3-5 hours, wherein both its half-life and its level in the blood fluctuate constantly in association with a wide variety of stressful diseases and stimuli. For example, the blood levels of Factor VIII correlate with the severity of DIC, eclampsia, and Raynoud's syndrome.

Furthermore, decreases in Factor VIII levels are associated with lowered blood viscosity and coagulability. Conversely, increases in Factor VIII levels are associated with increases in blood coagulability, in blood viscosity, in platelet activation, and in stress-related symptoms. Factor VIII's effects appear to be largely attributable to regulation of thrombin levels.

Both the half life and blood levels of Factor VIII constantly fluctuate in accord with SNS tone and activity levels as well as hypothalamic stimulation. Blood levels of Factor VIII appear to decline after anesthesia induction and ablation of psychic stress, accompanied by decreases in blood coagulability and viscosity, but then rise progressively with the onset of surgical tissue disruption. Blood levels of Factor VIII may remain elevated for at least eight days after surgical procedures, causing increases in blood coagulability, inflammation, and increased incidence of stress-related symptoms.

While Manucci et al, in the related art, first demonstrated that Factor VIII is released under nervous control in response to somatic pain, the present invention takes into consideration that pure psychic pain and stress, e.g., fainting or experiencing an earthquake without injury, are associated with sharp elevations in Factor VIII and fibrin as well as increased incidence of myocardial infarction, stroke, and angina, all of which are stress-related. Blood levels of Factor VIII may exhibit very sudden but short-lived increases, such as those following hard muscular exercise, fainting, or the injection of adrenalin; and they may exhibit sustained changes, such as those observed in pregnancy, diabetes, sepsis, inflammatory states, hyperthyroidism, and other stress-related conditions. Starvation depresses both SNS activity and Factor VIII levels, as does myxedema and moderate alcohol consumption.

Hypothalamic stimulation, which is known to control SNS activity levels, can cause either increases or decreases in Factor VIII blood levels. The increases or decreases depend on the part of the hypothalamus being stimulated. Hypothalamic stimulation has also been shown to cause endothelial damage and to accelerate atherosclerosis.

The VIIIC component of the Factor VIII complex is sex-linked, as the gene that produces it is located on the X chromosome. The VIIIC component mediates the conversion of prothrombin to thrombin, thereby activating the various effects of thrombin. The inherited inability to produce VIIIC is the cause of true hemophilia, the disease which afflicted the royal families of Europe.

VWF is produced by a somatic gene, stabilizes VIIIC, and extends VIIIC's half-life. In the complete absence of VWF, the half-life of VIIIC is so short as to be undetectable, resulting in a bleeding diathesis that cannot be distinguished from true hemophilia. VWF facilitates the adhesion of platelets to fibrinogen, fibrin, fibronectin, exposed collagen, and to one another so as to then facilitate the formation of white thrombi ("white clots") as a prelude to "red" clot formation. The present invention considers that this result is explained in VWF's ability to enhance and prolong VIIIC activity, thrombin production, and Factor XIII activation. Defects in the quality or quantity of VWF may result in bleeding problems, e.g., "von Willebrand's Disease," that vary widely in severity, presumably due to simultaneous impairment of both VWF and VIIIC functions. As noted previously, VWF may be a major factor in the operation of the Capillary Gate Mechanism.

The present invention considers that the stabilizing role of the VWF component of Factor VIII complex automatically extends the half-life of Factor VIII when large quantities of Factor VIII are released. This condition has important implications for the control of inflammation and the stress syndrome, because, once significant amounts of Factor VIII are released, Stress Mechanism activity may remain elevated regardless of subsequent stress-control measures and restoration of normal SNS activity levels. Further, the beneficial effects attributed to pre-emptive anesthesia of the present invention are utilized and explain much of the confusion that has bewildered research in the related art on the subject of stress.

Relating shear stress, turbulence, and mixing in the blood, the present invention considers that these factors play a role in both coagulation and atherosclerosis, but exact mechanism is lacking in the related art. Arterial blood flow appears to operate near a "transition zone," wherein small increases or decreases in shear stress (the force associated with the forward movement of blood, i.e., blood pressure per unit cross-sectional area of the blood vessel) result in large increases in turbulence and mixing. The cardiac cycle induces two peaks of turbulence in arterial blood flow. The first peak occurs in mid-systole, i.e., at the time of maximum shear stress. The second peak occurs in mid-diastole, wherein the blood flow momentarily reverses direction.

Turbulence is enhanced by hyperdynamic cardiac function, such as athletic activity, and is depressed by hypodynamic cardiac function, such as occurs in congestive heart failure. This is consistent with the observation that athletic conditioning retards atherosclerosis and hypodynamic heart function and that low activity levels, such as found in obesity, congestive heart failure, and myxedema, are associated with accelerated atherosclerosis. The effects of turbulence and mixing are also consistent with the observation that thrombophlebitis rarely occurs in arteries, but these effects are not uncommon in areas of stasis in the venous system, especially in the presence of hypercoagulability and hyperviscosity of blood, wherein levels of turbulence and mixing are reduced.

In the related art, researchers Bjorn H of et al. have published studies of fluid flow in pipes that demonstrate sharp increases in turbulence and mixing associated with sudden acceleration of flow rates. These studies, which employed laser beams and cameras to track microscopic tracer beads in water, demonstrated that a sudden increase in water flow rate in a pipe resulted in turbulent vortices that pushed sluggish water to the center of the pipe, creating a slow-moving streak down the center and fast-moving streaks around it. However, these related art studies do not address the particular problems associated with blood flow and the logistics of analyzing the blood flow. The present invention considers that pulsatile blood flow induces sharp increases in turbulence and mixing that occur most prominently along the walls of blood vessels in association with sudden increases in shear stress induced by cardiac activity. Such turbulence and mixing is expected to play an important role in preventing the deposition of blood elements on vessel walls and inhibiting coagulation in the present invention.

While Wettstein et al., in the related art, have demonstrated that defects in the quantity or quality of coagulation Factor XIII causes bleeding problems and that Factor XIII governs the formation of fibronectin cross-links to form a three-dimensional fibrin structure, the present invention considers that the physical properties of this three-dimensional structure induce "damping" of turbulence and mixing in blood; and Factor XIII's absence may disable the coagulation mechanism. While Kawasaki et al., in the related art, have demonstrated how fibrin strands, visible on electron micrographs, form attachments among various blood components as an integral part of the coagulation process, the present invention considers that these attachments may also induce "damping" of turbulence and mixing in blood or may synergize with the damping effects of three-dimensional fibrin matrix. While Alexandrov et al., in the related art, have demonstrated that ultrasound may inhibit blood clot formation and disrupt existing blood clots, the present invention considers that ultrasound may exert these effects by increasing turbulence and mixing in the blood.

BRIEF DESCRIPTION OF THE DRAWING

For better understanding of the present invention, reference is made to the below-referenced accompanying Drawing. Reference numbers refer to the same or equivalent parts of the present invention throughout the several figures of the Drawing.

MODE(S) FOR CARRYING-OUT THE INVENTION

Figure 1:
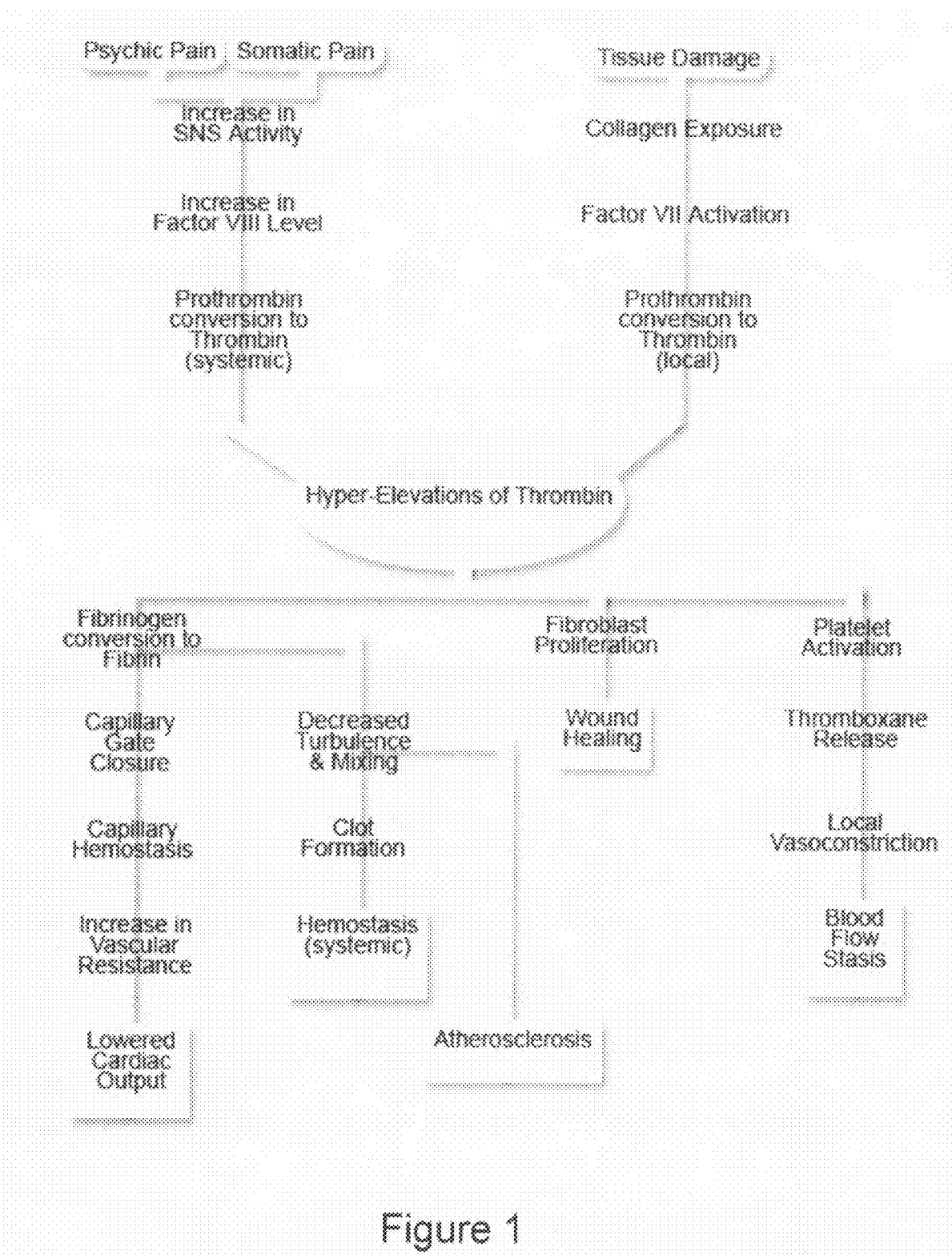
FIG. 1 is a diagram showing the effects of hyper-elevations of thrombin, in accordance with the related art.
Figure 2:
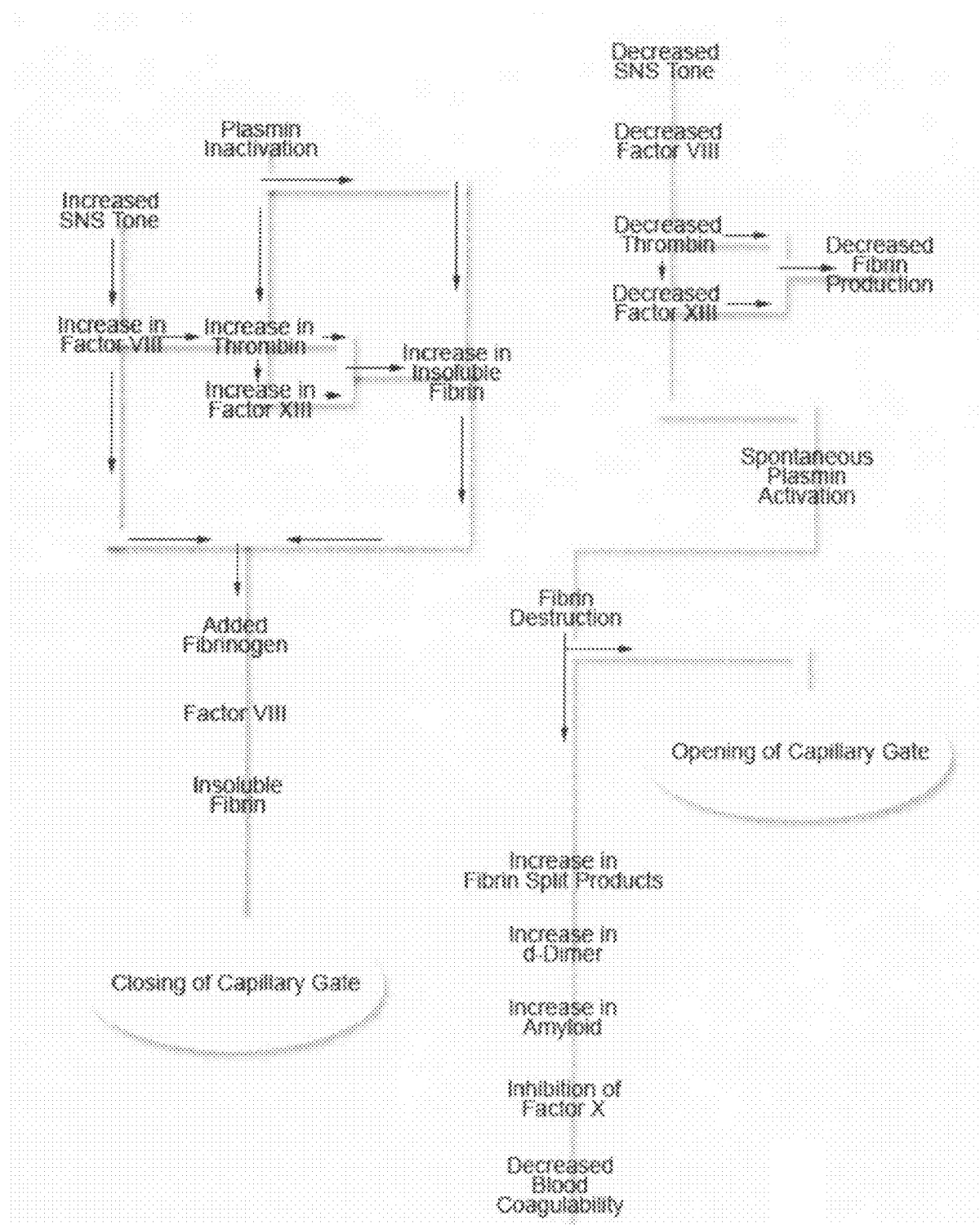
FIG. 2 is a diagram showing the events leading to, respectively, closing and opening of the capillary gate, in accordance with the related art.

The detailed description set forth below in connection with the appended drawings is intended as a description of presently-preferred embodiments of the invention and is not intended to represent the only forms in which the present invention may be constructed and/or utilized. The description of the mode(s) for carrying out the invention further sets forth the functions and the sequence of steps for constructing and operating the invention in connection with the illustrated embodiments. However, the same or equivalent functions and sequences may be accomplished by different embodiments which are also intended to be encompassed within the spirit and scope of the invention to be understood.

The present invention considers that blood turbulence and mixing induced by pulsatile blood flow, which is associated with sharp increases in mixing, inhibits blood coagulability by preventing blood components from adhering to one another to form clots. Further, the present invention considers that turbulence and mixing inhibits atherosclerosis by preventing toxic blood components from escaping suspension in the blood, from depositing on arterial surfaces, and from initiating the inflammatory response that results in atheroma formation.

With respect to fluid dynamics of blood in particular, turbulence and mixing vary inversely with viscosity. The present invention considers that chronic increases in blood viscosity, which may be caused by various factors, causes damping (decrease) of blood turbulence and mixing that accelerates atherosclerosis by allowing toxic blood components to escape suspension in the blood and to form deposits on arterial walls, thereby causing atheroma. The present invention considers that acute localized hyper-elevations of blood fibrin levels, under the combined control of Factors VII and VIII, locally increase blood viscosity, thereby resulting in decreases in turbulence and mixing that enable blood clot formation. When the fibrin matrix damps turbulence and mixing below a critical threshold, fibrin strands form spontaneously and connect various blood components to one another, thereby inducing even greater increases in viscosity, and thereby decreasing turbulence and mixing. As turbulence levels fall, additional fibrin strands form spontaneously and connect blood components into a clot. The present invention considers that extreme systemic hyperviscosity of the blood, causes systemic decreases in turbulence and mixing, thereby causing DIC.

Blood viscosity appears to be determined by a combination of factors, primarily including the following factors: (1) levels of the three-dimensional form of "insoluble" fibrin that are systemically regulated by Factor VIII; (2) levels of fibrinogen, which are normally stable and genetically-controlled, but may be elevated in chronic stress conditions such as smoking syndrome or diabetes; (3) red blood cell (RBC) mass being elevated in polycythemia vera, excessive erythropoiten, excessive transfusion with washed, packed RBC's, or a decreased in conditions such as the anemia of chronic uremia or iatrogenic hemodilution; (4) disease states such as leukemia or multiple myeloma, in which a profusion of white cells or immune globulin proteins cause increases in viscosity; and (5) hyperlipidemia.

Elevations of blood viscosity caused by any of these factors, or combinations of these factors, may pre-dispose a patient to problems associated with hypercoagulability, such as thrombophlebitis, accelerated atherosclerosis, and impaired capillary perfusion. Blood transfusions may cause elevations in blood viscosity and excessive transfusion of packed red blood cells can cause a form of DIC. Extreme stress-related elevations in blood viscosity due to abnormal elevations in blood levels of insoluble fibrin, such as those associated with sepsis, trauma, prolonged surgical procedures, or the HELLP Syndrome of eclampsia, precede and pre-dispose the onset of DIC syndrome, in which spontaneous widespread coagulation occurs. Over-transfusion with washed and packed red blood cells produces a similar situation.

Low blood viscosity states, such as those found in anemia caused by uremia or by acute blood loss and iatrogenic hemodilution, may exacerbate blood turbulence and mixing, thereby inhibiting blood coagulability so as to aggravate bleeding tendencies, as deemed by the present invention. This condition is more feasible than the "platelet washout syndrome" to which bleeding problems associated with massive blood loss, hemodilution, and uremia are commonly attributed.

Atherosclerosis is attributed to elevated blood levels or intake of cholesterol or lipids in the related art, but the evidence for this is questionable. Atherosclerosis is believed to correlate with advancing age, sedentary life-style, hemodynamic stress, increasing blood levels of Factor VIII, increases in blood viscosity, elevated fibrin, fibrinogen levels, and hypercoagulability, all of which are associated with increased blood viscosity, in accordance with the present invention. Anemia lowers blood viscosity and inhibits atherosclerosis, whereas elevated hematocrit accelerates it. Stressful diseases such as hyperthyroidism, which elevate blood viscosity, are associated with accelerated atherosclerosis despite normal or increased cardiac output and shear stress. Hypodynamic cardiac function, as in congestive heart failure and myxedema, is associated with accelerated atherosclerosis. Most chronic diseases are associated with accelerated atherosclerosis.

Atherosclerosis is typically counteracted by athletic conditioning, which increases turbulence and mixing. Several studies have demonstrated that moderate alcohol consumption, such as a glass of red wine every evening, retards atheroma formation and cardiovascular disease. The sedative effects of alcohol may also reduce psychic stress and reduce blood viscosity. Atherosclerosis may also be retarded by hemophilia and von Willebrand's Disease, although the patients of the latter disease retain the ability to heal wounds and form scabs. The present invention considers that these patients, having hemophilia and von Willebrand's Disease, are unable to produce the cross-linked form of fibrin.

In the related art, atheroma formation is believed to begin on the greater curvatures of the bifurcations of the arteries, i.e., wherein the shear stress is decreased, leading to the theory that low shear stress is the cause of atherosclerosis. However, the related art shear stress hypothesis is deficient in important respects. For example, the related art shear stress hypothesis fails to explain the acceleration of atherosclerosis that occurs in stressful conditions such as hyperthyroidism or direct hypothalamic stimulation, wherein both cardiac output and shear stress are maintained or increased. The related art shear stress hypothesis also fails to explain how regular, moderate, alcohol consumption, which is associated with low levels of shear stress, retards atherosclerosis.

The present invention considers that atherosclerosis is inhibited by blood turbulence and mixing, as opposed to merely shear stress. Low shear stress as well as low turbulence and mixing tend to occur under similar conditions. However, shear stress is minimally affected by viscosity, whereas turbulence and mixing may be sharply inhibited by elevations in viscosity and enhanced by reductions in viscosity. This consideration in the present invention better reflects the observation that accelerated atherosclerosis occurs in stressful conditions, such as hyperthyroidism, wherein the turbulent effects of hyperdynamic heart function may be negated by elevations in Factor VIII, which then increases blood viscosity by causing elevated levels of three-dimensional fibrin matrix in the blood. The present invention also better explains how the tranquilizing effects of moderate alcohol consumption retard atherosclerosis by decreasing psychic stress and SNS activity levels as well as lowering blood levels of Factor VIII, insoluble fibrin, and blood viscosity.

Somewhat surprisingly, Smoking Syndrome does not appear to be associated with elevated levels of Factor VIII and insoluble fibrin, although it is associated with other stress-related illnesses and may exacerbate their incidence or severity. However, Smoking Syndrome is consistently associated with elevated levels of blood fibrinogen, platelet reactivity, RBC mass, and blood viscosity. The present invention considers that smoking induces increases in blood viscosity by increasing both RBC mass and blood fibrinogen levels and that the increased viscosity causes decreased turbulence and mixing in the blood, which is then responsible for the acceleration of atherosclerosis and heart disease that is strongly associated with Smoking Syndrome.

Nicotine is known to have powerful sedative/hypnotic and stress-opposing effects. The present invention considers that nicotine reduces psychic stress and thereby reduces blood levels of Factor VIII, thereby possibly explaining the normal levels of Factor VIII observed in smokers. The effects of nicotine may oppose and offset the otherwise stressful effects of smoking. This is consistent with the observation that smoking reduces the severity of symptoms in eclampsia, wherein the tranquilizing effects of nicotine may reduce Factor VIII levels and blood viscosity. This effect may be similar to the protective effect of moderate alcohol consumption. These sedative effects, in and of themselves, may mitigate the release of Factor VIII and assist in preventing acute increases in blood viscosity due to the fibrin matrix, but the chronic increase in blood viscosity caused by elevated hematocrit and fibrinogen may dominate the beneficial effects of nicotine.

Regarding Factor VII, coagulation, wound healing and apoptosis, a substance or a mechanism has long been suspected, but never verified, that localizes and controls the inflammatory response, "white clot" and subsequent "red clot" formation, fibroblast proliferation, and wound healing.

Factor VII is believed, in the related art, to be activated by exposed collagen and to cause conversion of prothrombin to thrombin. Factor VII is also believed, in the related art, to activate the "intrinsic" pathway. The present invention considers that Factor VII is a locally-acting stress agent that synergizes with the systemic effects of Factor VIII to cause hyper-elevations of thrombin at the site of tissue disruption, thereby governing localized clot formation and wound healing.

The present invention considers that "tissue factor" is collagen or a portion of the collagen molecule. Collagen, a ubiquitous protein that is a basic structural component of all larger blood vessels, is normally separated from flowing blood by the delicate vascular endothelium, which is only one cell layer thick. Traumatic stress that disrupts the vascular endothelium immediately exposes underlying collagen to flowing blood and activates Factor VII.

Factor VII has been successfully employed via intravenous infusion as a substitute for Factor VIII to treat hemophilia and trauma, but its normal thrombin-elevating effects are believed to be primarily local, whereas those of Factor VIII appear to be systemic. Like Factor VIII, the half-life of Factor VII is very short; and it must be administered as an infusion to treat hemophilia. The origin of Factor VII appears to be hepatocytes, and its function is vitamin K dependent. Like fibrinogen, the level of Factor VII in blood is normally stable and genetically controlled, but may be elevated in chronic stress conditions such as diabetes. If administered in excessive quantities, Factor VII causes hypercoagulability of blood, similar to Factor VIII. Deficiencies in the quality or quantity of Factor VII are rare, but devastating.

Normally, thrombin elevation, caused by both Factor VII and Factor VIII, is required for effective clot formation. In rare circumstances, such as severe sepsis or eclampsia, extreme stress-related elevations in Factor VIII may cause severe systemic hypercoagulability that pre-disposes to DIC. However, with the exception of venous thrombophlebitis, the hypercoagulability induced by Factor VIII is not ordinarily associated with clot formation in the absence of tissue disruption and Factor VII activation. Likewise, in the absence of Factor VIII, Factor VII does not appear to be produced in adequate quantities to initiate clot formation, as evidenced by the absence of clot formation in hemophilia. Normal coagulation appears to involve the combined effects of Factors VII and VIII in response to a combination of SNS activation and collagen exposure to flowing blood, which, in turn, elevates local thrombin levels and initiates "white clot" formation and subsequently governs the transition of "white clot" to "red clot" as collagen is repeatedly re-exposed and Factor VII is re-activated.

Subsequent re-exposure of collagen due to deterioration of the "red clot" causes persistent re-elevations of thrombin levels at the site of injury that initiate and sustain the inflammatory response, fibroblast proliferation, and collagen production, thereby governing the wound-healing process. Factor VII may also control cell migration via thrombin. As wound healing proceeds to completion, collagen is ultimately sealed from exposure to flowing blood, thrombin levels decline, and the acute phase of wound healing ends. The present invention considers that apoptosis is caused by declining thrombin levels that occur during the resolution of the acute phase of the wound healing process. That Factor VII plays a major role in regulating the wound healing process is consistent with the fact that wound healing and scab formation appear to remain near-normal in the absence of Factor VIII.

While, it is known in the related art that proliferating fibroblasts are exquisitely sensitive to hypoxia and acidosis, which may cause inadvertent apoptosis, and that the early stages of capillary formation taking place in the wound healing process may be disrupted by a variety of stressful stimuli, this presumption only explains the poor wound healing and increased incidence of wound infection associated with uncontrolled surgical stress. The present invention considers that proliferating fibroblast cells are inherently fragile, are susceptible to apoptosis, and are critically dependent on adequate, but not excessive, levels of thrombin to multiply and function correctly.

With respect to Virchow's Triad more than 150 years ago, Rudolf Virchow stated this famous "Triad" of postulates or factors that must be present in order for blood coagulation to occur: (1) blood flow stasis; (2) hypercoagulability of blood; and (3) tissue crushing. The understanding of how coagulation occurs has changed little since Virchow's time, and the mechanisms of these postulates have yet to be explained in the related art.

Although it seems intuitively logical, the "Cascade" theory of blood coagulation in the related art is dauntingly, complex and confusing and exhibits numerous shortcomings and inconsistencies. The Cascade Theory fails to provide a clear explanation of the postulates of Virchow's Triad, but implies that enzymatic blood proteins engage in a series of confusing and cross-related interactions that culminate in the formation of fibrin, but offers no explanation of how fibrin might control either hemostasis or localized clot formation. Cascade Theory offers few clues as to how such a potent system might cause disease or be affected by it. Cascade Theory fails to explain the perturbations in blood viscosity, coagulability, and rheology that are commonly associated with disease processes. These are but a few of its more obvious shortcomings. Worse yet, many of the laboratory tests that have been used both to study the Cascade Theory and to perform clinical testing are inadequately standardized, indirect in nature, or simultaneously test multiple reactions in the related art; and, thus, they may produce confusing or contradictory results. For example, published studies have variously attributed direct platelet activation to thrombin, Factor VIII, Factor VII, and collagen. Inhibition of the conversion of plasminogen to plasmin has been attributed to both thrombin and "Plasmin Activator Inhibitor-1" (PAI-I). Factor VII activation has been confusingly attributed to both exposed collagen and "Tissue Factor," when both "Tissue Factor" and collagen would appear to be present in the same extravascular location, suggesting that they might be one and the same. The effect of this confusion may be to discourage logical and systematic investigation in the related art.

Stress Theory, in contrast to Cascade Theory, may offer a simple explanation of Virchow's Triad as follows: (1) injury causes a combination of psychic and somatic pain and stress that cause SNS activation and the release of Factor VIII, causing systemic elevations in thrombin; (2) disruption of the vascular endothelium (tissue crushing) causes Factor VII activation at the site of injury that produces additional elevations of thrombin in the immediate vicinity of injury; and (3) the localized hyper-elevated levels of thrombin due to the combined effects of Factors VII and VIII cause platelet activation and the release of thromboxane, which then causes intense vasoconstriction and stasis of blood flow in the immediate vicinity of injury as well as elevations in levels of insoluble fibrin that induce hypercoagulability of blood that results in visible clot formation.

Prevailing theories of the cause of malignancy usually involve the assumption of genetic damage induced by radiation, viruses, or other factors that cause cells to undergo a malignant change. The present invention considers an alternative explanation, i.e., that the cause of malignancy is prolonged, stress-related hyper-elevation of systemic and local thrombin levels that over-stimulate wound-healing cell proliferation, thereby causing proliferating wound cells to invade normal tissues and provoke a self-sustaining stress response. The present invention considers that the resulting stress response maintains elevated thrombin levels so as to support continued cell proliferation and invasion. This assertion is consistent with the observation that chronic ingestion of toxic chemicals is associated with increased rates of various types of malignancies in various locations, but painting the same chemicals on skin surface causes greater increases in the incidence of cancer at the application site than systemically. This assertion is also consistent with the association between malignancy and stressful conditions such as diabetes and morbid obesity.

Malignancy has been known to be associated with sustained and elevated stress, such as prolonged osteomyelitis infection and sepsis, chronic exposure to toxic chemicals, or chronic tobacco abuse in the related art. Malignancy is increased in the aftermath of major surgery, a stressful event. Cancer is typically accompanied by increases in Factor VIII and thrombin, and in turn, accompanied by increases in blood viscosity and coagulability, the relationship being possibly one of both cause and effect. Thrombin has been demonstrated to promote both mitosis and malignancy. Thrombin has been demonstrated to stimulate proliferation of brain astrocytes and may be directly associated with astrocytoma. Thrombin has also been shown to play an important role in lung and colon adenocarcinoma. Elevated levels of thrombin may be necessary for cancer cell survival. Elevations of Factor VII also promote malignancy. Anti-thrombin medications have been demonstrated to induce apoptosis and enhance the effectiveness of other cancer treatments, suggesting that a combination of intense anti-stress and anti-thrombin measures might offer an improved technique for inducing apoptosis so as to treat malignancy. The present invention recognizes that conventional cancer therapies in the related art, including surgery, chemotherapy, and radiation therapy, are innately counter-productive, in that these related art therapies cause stressful stimuli that tend to aggravate the malignant process for which they are intended to cure.

In relation to pharmacology and the Capillary Gate Mechanism, Stress Theory might offer an improved understanding of the mode of action of vasoactive drugs that are commonly employed as anesthesia adjuncts and might lead to more judicious use of these agents. The terms "vasopressor," "vasodilator," and "vasoconstrictor" imply that such agents owe their effects to muscular constriction or relaxation of the lumens of arteries, arterioles, veins, and venules. However, these terms may be misnomers. Stress Theory and research evidence suggests that "vasodilator" drugs such as nitroprusside, nitroglycerine, epsilon-aminocaproic acid (EACA), magnesium sulfate ($MgSO_4$), and furosemide interfere with the conversion of "soft" fibrin to "insoluble" fibrin or induce fibrinolysis, so as to prevent the closure of the Capillary Gate Mechanism, to reduce systemic vascular resistance, and to lower blood pressure. The therapeutic effects of these drugs may be explained by their ability to improve capillary bed perfusion. "Vasoconstrictor" drugs, such as epinephrine, vasopressin, and ionized calcium, may promote the conversion of "soft" fibrin to "insoluble" fibrin, thereby facilitating closure of the Capillary Gate Mechanism, thereby increasing systemic vascular resistance, and thereby increasing blood pressure. Thus, "vasopressors" may enhance CFS effects, while "vasodilators" may oppose them. This may better explain the mode of action and many of the side-effects associated with excessive use of "vasopressor" drugs.

Calcium channel blockers such as Nifedipine and Verapamil are known to lower blood levels of $Ca^+$, and, thus, may exert their effects by interfering with the formation of insoluble fibrin. They have been used successfully to treat Raynoud's Syndrome. They are known to reduce blood pressure, blood viscosity, and systemic vascular resistance as well as to preserve cardiac output. They may inhibit atherosclerosis and tissue hypertrophy induced by stress (both effects being mediated by thrombin). They have also been associated with bleeding problems. In contrast, calcium preparations have been used to control bone bleeding. Calcium channel blockers have also been shown to reduce myocardial infarct size in rats, to augment bowel and myocardial perfusion in shock states, and to prevent the "no-reflow" phenomenon that sometimes follows successful angioplasty procedures. They are associated with beneficial effects on atherosclerosis. The present invention considers that "no-reflow" is a manifestation of CFS in cardiac tissue. Calcium Channel blockers also appear to interfere with platelet activation. They may exert these therapeutic effects by interfering with the elevation in $Ca^+$ levels associated with thrombin actions.

Local anesthetics have well-recognized systemic anesthetic, anti-inflammatory, and anti-coagulant effects; however, the anti-coagulant effects and anti-inflammatory effects are unexplained. Their anti-arrhythmic effects are presently attributed to their supposed ability to stabilize nervous conduction pathways in the heart. The present invention comprises an alternative approach and considers that local anesthetics anesthetize the exposed nerve endings of the SNS in the vascular endothelium and prevent the release of Factor VIII, that local anesthetics achieve their anti-arrhythmic actions by reversing CFS and tissue ischemia in nervous, pulmonary and cardiac tissue, thereby restoring stable function, and that the anti-inflammatory and anti-coagulant effects of local anesthetics are likewise explained by inhibition of Factor VIII release and lowered levels of thrombin activity. When administered via conduction anesthetic techniques, the local anesthetics may block sympathetic nerves directly, also preventing the release of Factor VIII, plus small amounts may escape into systemic circulation and exert additional effects.

Surgeons frequently employ mixtures of local anesthetics and epinephrine to simultaneously control surgical pain and to effect hemostasis in the related art. In most cases this approach works well, but in certain patients the presence of local anesthetics is associated with persistent "oozing." There have been reports of serious hematoma formation that has accompanied the use of local anesthetic injections of tissues. The present invention considers that these occasional manifestations of inadequate hemostasis are caused by mild cases of von Willebrand's Disease, in which the effects of local anesthetics further inhibit the already marginal function of the Factor VIII molecule and prevent closure of the Capillary Gate, thereby causing failure of capillary hemostasis.

Streptokinase and urokinase appear to exert their effects by enhancing the operation of plasmin. Their benefits may derive from their ability to promote the dismemberment of the three-dimensional insoluble fibrin matrix by plasmin, to reduce systemic hypercoagulability of blood, and to cause opening of the Capillary Gate and reduction of CFS. The sudden hypotension associated with large doses of these drugs may be explained by sudden, widespread opening of the Capillary Gate that causes a decrease in systemic vascular resistance. This circumstance may also explain the "re-perfusion arrhythmias" that are associated with these drugs, which may be caused by a "steal" phenomenon of blood flow at the expense of compromised tissues. The therapeutic benefits associated with these drugs may derive primarily from their ability to reverse CFS during the early stages of evolving MI, as thrombosis appears late in the infarction process.

Beta-blocker drugs such as propranolol are presently believed to exert their benefits by lowering heart rate and increasing diastolic filling time. However, these drugs are also known to interfere with platelet activity, lower blood fibrinogen levels and lower blood levels of Factor VIII. Thus, the benefits of these drugs may derive primarily from their ability to inhibit the Stress Mechanism.

Aspirin is presently thought to produce its therapeutic effects by inhibiting platelets in the related art. Its inhibition of other elements of the coagulation process is poorly appreciated; and its beneficial effects may derive primarily from its ability to inhibit CFS rather from platelet effects.

The "Fight or Flight" Stress Syndrome described by Hans Selye in the related art may be explained in terms of stress-related effects, e.g. hypercoagulability of blood, capillary hemostasis, increased systemic vascular resistance, elevated blood pressure, etc., that are activated by psychic stress, stimulus, and the release of stress hormones, including Factor VIII, in advance of physical injury so as to minimize blood loss in the event of subsequent injury and to enhance the success of fighting or escaping. The survival benefits of such a mechanism are self-evident; and abundant evidence exists that SNS activity levels and blood levels of Factor VIII can be elevated by fear and psychological stress, sometimes accompanied by pathological manifestations of stress such as myocardial infarction, stroke, and sudden death.

In contrast, the "Surgical Stress Syndrome" may be explained by the inadvertent elevation of SNS activity levels and release of Factor VIII due to inadequately controlled somatic stress, despite ablation of the patient's psychic stress and conscious awareness of pain via the use of sedative/hypnotic anesthetic agents. Prevailing techniques for administering general anesthesia ("Traditional" Technique) rely heavily on combinations of inhalation agents and muscle relaxants to achieve satisfactory operating conditions, but these techniques do not inhibit the effects of somatic stress. SNS tone, SNS activity levels, and blood levels of Factor VIII, blood coagulability, platelet activity, and blood viscosity decline on induction of anesthesia and ablation of psychic stress and awareness, but then they begin to rise after surgical stimulus and the onset of somatic stress. These levels do not reach peak levels until several hours after completion of the surgical procedure. These levels do not return to normal levels for at least several days. Psychic stress, associated with anesthesia emergence and restoration of the conscious awareness of pain, may add to the stressful activation of SNS activity levels caused by tissue disruption. Stress-related morbidity and mortality coincide with the rise in Factor VIII blood levels.

Sufficiently activated, Factor VIII levels may remain elevated for at least eight days after surgery, i.e., long after SNS activity levels have returned to normal; and these Factor VIII levels may be resistant to subsequent pain control measures. This prolonging Factor VIII's half-life and its insensitivity to subsequent stress-control measures may be explained by the preserving and stabilizing effects associated with the release of large amounts of VWF and/or CNS "Wind-Up." The elevation in Factor VIII levels is mirrored by clinical manifestations of the Surgical Stress Syndrome, including vasomotor instability, tachycardia, hypertension, fever, mental disorientation, stroke, dysrhythmias, myocardial infarction, bowel ileus, poor wound healing, wound infection, and death.

Both the rise in Factor VIII levels and the manifestations of surgical stress may be mitigated by the pre-emptive use of conduction anesthesia, local anesthetic infiltration, generous dosage with opioids, and other stress control techniques that inhibit the release of Factor VIII; however, the present invention recognizes that any lapse of stress control which allows SNS activation during, or for several hours after, surgical tissue disruption may risk causing sustained elevations of Factor VIII that may subsequently resist control.

The present invention recognizes that the pathological effects associated with the Surgical Stress Syndrome are primarily caused by uncontrolled elevations of circulating Factor VIII, wherein Factor VIII causes elevated thrombin activity, hyperviscosity of the blood, hypercoagulability of blood, systemic inflammation, and prolonged and widespread closure of the Capillary Gate Mechanism, thereby resulting in cellular hypoxia and tissue damage in capillary beds, i.e., Capillary Fibrin Stress (CFS). CFS may explain the increased incidence of stress-related problems in geriatric patients, whose decreased cardiac index, increased blood levels of Factor VIII, and senescent capillary beds that having perfusion defects, may render them more vulnerable to CFS, thrombophlebitis, and atherosclerosis than younger patients. The foregoing observation is also consistent with the fact that most stress symptoms are closely associated with vital organs that require uninterrupted perfusion, such as the brain, the bowel, the heart and the kidneys.

Prolonged, low-grade activation of the Stress Mechanism after surgical procedures may cause persistent systemic inflammation and explain the increase in malignancy, mortality and morbidity in the distant aftermath of surgery, as noted by Terri Monk et al. in the related art. This finding strongly correlates with the "traditional" technique of general anesthesia that relies primarily on inhalation agents and muscle relaxants and does not effectively inhibit somatic stress.

Stress Theory suggests that a new Theory of Anesthesia as well as alternative anesthetic goals and strategies are needed to optimize surgical outcome. Previous attempts in the related art to develop theories of anesthesia are confined to explaining the reversibility of the conscious awareness of pain may be inadequate. The present invention recognizes that anesthesia may be analogous to stress control. The optimal role of the anesthesiologist may be to protect his patient from stressful stimulus, whenever possible, and to employ adequate doses of analgesics (local anesthetics and opioids) to control the effects of somatic surgical stress in addition to the traditional use of hypnotics to ablate conscious awareness and the effects of psychic surgical stress. Optimal outcome may require pre-emptive uninterrupted measures to control the effects of both psychic and somatic surgical stress and to prevent hyperactivation of the Stress Mechanism. The term "anesthesia" which denotes "loss of sensation" may be inadequate to describe this role. The loss of sensation is termed "antinociception anesthesia," in accordance with the present invention.

Traditional approaches to anesthesia rely primarily on combinations of inhalation agents and muscle relaxants. This combination provides good surgical conditions and apparent safety and predictability; however, Stress Theory suggests that the persistent elevations in systemic vascular resistance as well as blood viscosity and coagulability, associated with this technique may be caused by inadequately controlled somatic stress that may increase risk. The associated increases in blood pressure are customarily treated with increased concentrations of inhalation agent or intravenous hypnotic agents in the related art belief that hypnotic agents reduce sympathetic tone and activity levels. However, neither hypnotics nor muscle relaxants prevent the release of hormones in response to somatic stress; and large doses of hypnotics are known to cause direct myocardial depression. Hypnotics may, thus, reduce blood pressure by depressing cardiac output rather than by controlling SNS activity. Low blood pressure is accordingly viewed with alarm by anesthesiologists, who regard it primarily as a warning of dangerous cardiac depression caused by anesthetic agents. In consequence, opioids and conduction anesthesia techniques are often avoided or used with great caution due to their tendency to cause hypotension when combined with hypnotics. In addition, traditional anesthesia techniques typically employ deliberate hypocarbia, which may be inherently counterproductive and which may cause dangerous respiratory depression in the presence of generous opioid dosage. This circumstance further discourages the use of opioids.

Stress Theory suggests that blood pressure may be an inadequate and misleading standard for anesthesia monitoring and record-keeping purposes. Hypotension in the presence of the "traditional" technique of general anesthesia, wherein uncontrolled somatic stress routinely causes elevations in systemic vascular resistance is properly regarded as a warning of cardiac depression. In contrast, moderate hypotension in the presence of modern stress control techniques that employ opioids and local anesthetics in doses adequate to control somatic stress may signal the opening of the Capillary Gate, the reduction in systemic vascular resistance, the improved capillary bed perfusion, and the establishment of effective and desirable stress control conditions. This effect has been demonstrated most clearly in the case of combined epidural/general anesthesia techniques, wherein increased tissue perfusion and oxygenation, together with improved outcome and reductions in the incidence of symptoms of Surgical Stress have been demonstrated despite significant reductions in blood pressure. Similar improvements in outcome, together with synergistic reductions of SNS tone and blood pressure, appear to occur with combinations of inhalation agents and opioids. A similar effect may explain successful therapeutic regimens for congestive heart failure that combine fibrinolytic agents such as NTP and NTG that lower systemic vascular resistance (and blood pressure) with inotropes such as dopamine that increase cardiac output. Reductions in blood pressure may reflect benefit under such circumstances. Alternative means of evaluating perfusion and oxygenation may offer a monitoring standard that is more useful and less confusing than blood pressure.

Figure 3:
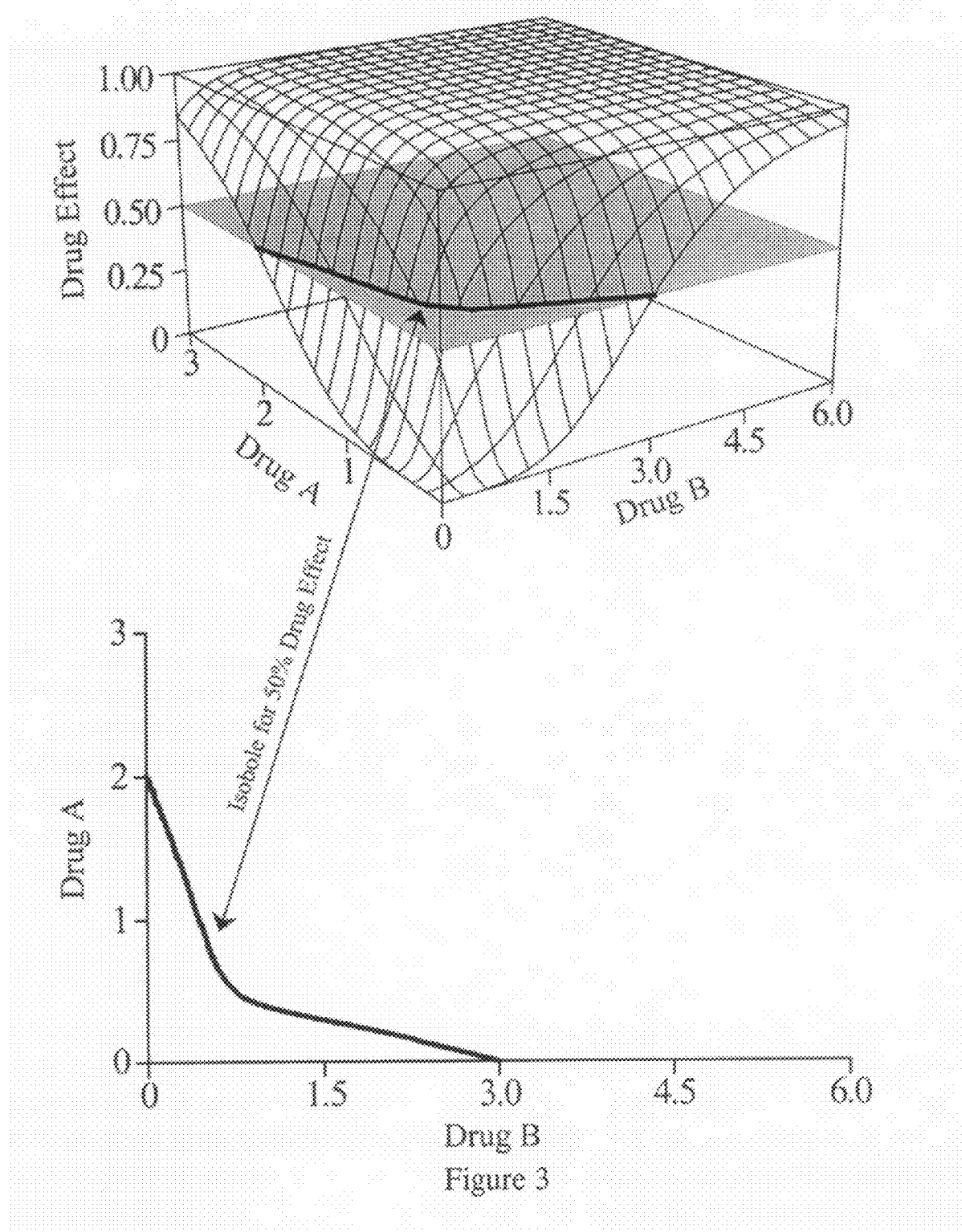
FIG. 3 is a graph showing the sigmoid concentration-response relation for three fixed ratios of drug A and drug B. The effect for any combination of drug A and drug B is described by the response surface, in accordance with the present invention.

In the present invention, general anesthetic approaches comprising of a two-drug process involving combinations of an analgesic (opioid or local anesthetic) and a hypnotic (such as an inhalation agent) that synergize each other's effects via their respective abilities to depress SNS and Central Nervous System (CNS) activity. This can be visualized in the form of a three-dimensional "bologram" (FIG. 3). Opioids and local anesthetics produce a marked reduction in the level of hypnotic required, and vice-versa. The relationship is highly non-linear, and neither type of agent produces satisfactory results when used alone. This synergism of hypnotics and analgesics is consistent with Stress Theory, which suggests that psychic and somatic stress cause SNS activation via semi-autonomous pathways.

These scientific principles may be exploited to optimize desirable drug effects, to minimize those not desired, and to devise an antinociceptive general anesthetic strategy that may optimize outcome in the manner of combined epidural-general techniques. Opioids control somatic stress in a dose-related manner, but also cause minimal depression of cardiac output. Inhalation agents produce optimal control of psychic stress in below minimum alveolar concentration ("MAC") that ablate awareness, but large concentrations progressively depress cardiac output. Therefore, small concentrations of inhalation agents may be combined with generous doses of opioids to achieve simultaneous control of both somatic and psychic stress, thereby theoretically optimizing control of SNS activity levels and the Stress Mechanism, with minimal direct depression of cardiac output, in accordance with the present invention. The interaction may also be exploited to accelerate anesthetic induction and emergence, as well as to reduce the need for muscle relaxants which operate via a separate mechanism and do not synergize the effects of either opioids or hypnotics. The respiratory depression that may accompany this technique can be easily managed with common respiratory support techniques that allow mild hypercarbia to offset the respiratory effects of opioid and encourage cardiac output.

In FIG. 3, the leftmost and rightmost edges of the surface represent the sigmoid concentration-response relation for drug A and drug B, respectively. In accordance with the present invention, the three radial lines on the surface show the sigmoid concentration-response relation for three fixed ratios of drug A and drug B, respectively, in accordance with the present invention. The effect for any combination of drug A and drug B is described by the response surface. The 25, 50, and 75% effect isoboles are shown.

Stress Theory might inspire fresh approaches to anesthesia. Intravenous lidocaine infusion, a once-popular anesthetic technique in North America, was abandoned after the introduction of Halothane in the related art. Surviving descriptions of the technique suggest that the lidocaine dosage needed to achieve adequate analgesia was associated with a pronounced cutaneous flush and mild hypotension that might be explained by the reduction of Factor VIII blood levels and widespread opening of the Capillary Gate. The lidocaine infusions have been shown to control thrombophlebitis and to reduce minimum alveolar concentration ("MAC"), which may be explained by such infusions' ability to inhibit somatic stress and the release of Factor VIII. However, they might offer a relatively safe and effective technique for achieving antinociceptive anesthesia if combined with hypnotic agents and respiratory support, in accordance with the present invention.

The following text describes the interpretations of selected diseases and syndromes in terms of Stress Theory and illustrate how the Theory may provide simplified and improved explanations of observed phenomena, in accordance with the present invention.

EXAMPLE 1

SIRS, ARDS, & Multi-Organ Failure

Systemic Inflammatory Response Syndrome (SIRS) has five identified components: (1) vasodilation, (2) increased microvascular permeability, (3) increased leukocyte and (4) platelet activation and (5) adhesion, and hypercoagulability. SIRS tends to be associated with conditions of stress, such as trauma, sepsis, pancreatitis, and burns. Multi-Organ Failure Syndrome (MOFS), also a Critical Care phenomenon associated with sepsis and trauma which is frequently observed in the Intensive Care Unit, is associated with the same types of extreme stress and exhibits similar symptoms. These syndromes may be closely related stress states which are caused by activation of Factors VII and VIII. SIRS may be explained by relatively greater activation of Factor VII, causing inflammatory effects to predominate, and MOFS may be explained by relatively greater activation of Factor VIII, thereby causing the effects of hyper-elevations of blood fibrin levels to predominate. Alternatively, SIRS may represent the prelude to MOFS or a lower-grade activation of the Stress Mechanism. Extreme activations of the Stress Mechanism and elevations of circulating insoluble fibrin may explain the increased incidence of DIC and the fibrin deposits that appear in vital organs in MOFS.

ARDS is characterized by elevations in Factor VIII, is strongly associated with DIC, appears to be part of Multi-Organ Failure Syndrome, and serves as a prototypical example of fibrin-induced organ damage that disrupts the function of kidneys, bowel, liver, and other organs in severe stress states. Massive deposits of fibrin have been documented in pulmonary capillaries in ARDS. The present invention recognizes that stress-related fibrin deposits in alveolar capillaries are the cause of the ARDS syndrome. Because of the large capillary reserves that exist in normal lung, the onset of ARDS tends to be occult and insidious. Pulmonary vascular resistance is normally very low, and the accumulating fibrin may cause few noticeable symptoms until fibrin deposits have accumulated beyond a critical threshold, which in turn, causes increased pulmonary vascular resistance, pulmonary perfusion pressures, and right heart failure. This would explain the apparent sudden onset of clinical symptoms that commonly inspires ineffective and potentially counter-productive efforts to treat the syndrome using ventilation techniques. Surviving patients often suffer residual pulmonary fibrosis and permanent lung damage as the stress mechanism consolidates the fibrin deposits into sclerotic lesions that reduce capillary reserve. The present invention recognizes that a similar stress phenomenon, resulting in acute thrombin-mediated deposition of fibrin in lung capillaries combined with thrombin-mediated fibroblast activation, may largely explain asthma, High Altitude Pulmonary Edema (HAPE), cor pulmonale, the pulmonary manifestations of acute CHF, and other lung pathologies.

EXAMPLE 2

Shock

The present invention recognizes that shock states, including cardiogenic shock, septic shock, and hypovolemic shock, are caused by combinations of stress-related closure of the Capillary Gate which in turn cause increased systemic vascular resistance and CFS and low cardiac output. The SNS may regulate closure of the Capillary Gate so as to direct limited cardiac output preferentially to vital organs, such as the heart and brain to preserve life, while other tissues may suffer hypoxic damage due to exaggerated CFS under such circumstances. Shock states are associated with elevations of SNS tone, systemic vascular resistance, Factor VIII, blood viscosity and coagulability, and blood levels of insoluble fibrin. "Second Tier" organs such as kidneys and bowel that normally require high perfusion rates may be particularly vulnerable to CFS under such circumstances; and the stress-related elevations in blood levels of insoluble fibrin may explain the renal "casts", acute tubular necrosis, and bowel ileus that occur in such conditions. The present invention recognizes that the heart and brain are relatively resistant to the effects of CFS, but are not immune. Therefore, circumstances may be partly explained by the activity of astrocytes in the brain which may mediate the release of both fibrinolytic and fibrin-enhancing substances from the vascular endothelium that preserve brain capillary blood flow in hypotensive states. Astrocytes may be specialized neurons that control the release of stress-related hormones from the vascular endothelium that regulate the Capillary Gate in addition to the Stress Mechanism. The activity of astrocytes may thus largely explain "cerebral autoregulation."

EXAMPLE 3

Eclampsia

Normal pregnancy is a stressful condition that is associated with above-normal levels of Factor VIII and blood coagulability. It is associated with other stress-related conditions, such as diabetes, and may aggravate these conditions. Eclampsia is a stress state that involves levels of blood coagulability and Factor VIII that are elevated above those of normal pregnancy; and the severity of eclamptic symptoms mirrors the elevations in Factor VIII and blood coagulability. A common source of additional stress that may convert a normal pregnancy into an eclamptic state is sepsis resulting from pyelonephritis. The risk of eclampsia is increased by the presence of other stress states, such as diabetes. In the most severe manifestation of eclampsia, known as HELLP Syndrome, a severe risk of DIC exists that may be initiated by amniotic fluid embolus; and visible fibrin deposits appear in various organs, thereby causing disturbed organ function. Fibrin deposition on placental villi interferes with fetal growth and development and may cause miscarriage. Fibrin deposits in the liver can disturb liver function and cause the organ to swell and burst, even with fatal consequences.

The present invention recognizes that occult fibrin deposits in the renal arterioles disturb juxtaglomerular apparatus function and cause activation of the renin-angiotensin-aldosterone reflex in a manner analogous to that observed in the classical Goldblatt kidney. This circumstance may explain the severe water retention, cerebral and peripheral edema, as well as electrolyte disturbances observed in eclampsia. The present invention considers that a similar stress mechanism explains the so-called "essential" hypertension and may be the major cause of renal failure.

Magnesium sulfate (MgSO4), the most effective treatment for eclampsia, has powerful anticoagulant properties, and reduces blood fibrin levels. MgSO4 has recently been shown to be surprisingly effective in the treatment of pheochromocytoma symptoms, perhaps via similar properties as those required for treating eclampsia. Magnesium deficiency is associated with arrhythmias, hypertension, neural, disorders, psychiatric disturbances, and sudden ischemic death. The present invention recognizes that the therapeutic effects of MgSO4 are explained by its ability to interfere with the formation of insoluble fibrin, open the Capillary Gate, and inhibit CFS. The present invention comprises MgSO4 as effective treatment for other acute manifestations of stress, such as ARDS and multi-organ failure.

EXAMPLE 4

Diabetes

Diabetes is a stressful condition in which cellular glucose deprivation causes SNS activation and elevations in blood levels of stress hormones, including glucagon and Factor VIII. This condition is opposed by parasympathetic activity. The effects of glucagon cause elevations of blood glucose that characterize the disease, but evidence that elevated levels of blood glucose cause tissue damage is lacking. The elevation of stress hormones appears to interfere with the transport of glucose into cells, thereby causing additional stress and further aggravating the problem in the form of a "vicious cycle." The chronic stressful stimulus causes persistent elevations in fibrinogen, fibrin, viscosity, and coagulability that disturb blood rheologyand microcirculation. Chronic CFS may explain the inexorable tissue and organ damage that occurs over time. Careful management of cellular hypoglycemia using insulin and measures to alleviate stress, and direct treatments that reduce blood viscosity have been shown to improve capillary blood flow and diabetic symptoms.

Amyloidosis may play an important role in diabetes as a cause and/or possibly an effect. Amyloidosis is associated with increased fibrin turnover, which is characteristic of stress states. A strong correlation exists between diabetes and Alzheimer's Disease, which is caused by amyloid deposits. Evidence exists that amyloid protein may be involved with the destruction of insulin-producing cells in the pancreas.

The known increases in morbidity and mortality associated with the treatment of diabetes using sulfonamide compounds may be that these drugs cause a decrease in blood glucose levels, thereby aggravating stressful cellular glucose starvation, SNS activation, and glucagons release. The observed increase in morbidity and mortality associated with these drugs may be due to their tendency to activate the Stress Mechanism.

EXAMPLE 5

Future Directions

While Stress Theory involves numerous avenues of research and treatment in the related art, additional research is needed to challenge Stress Theory and clarify its mechanisms. Animal research is needed to determine the most effective anesthetic approach to maintain capillary perfusion and tissue oxygenation. The possible role of other enzymatic proteins that are associated with the coagulation process must be evaluated with respect to the Theory. For example, Factor V Leiden, which appears to oppose the effects of thrombin and Factor VIII, may function to maintain the Capillary Gate in an "open" state, except under a condition of acidosis or low calcium. The role of Factors IX ("Christmas Factor") and X may also be clarified.

Studies are needed to evaluate the possibility that combinations of anti-thrombin agents, Factor VII inhibitors, and stress control techniques, such as lidocaine infusions, may offer more effective treatment of malignancy, rheumatoid diseases, eclampsia, diabetes, and other pathologic manifestations of Stress Mechanism hyperactivity. Rheopheresis therapies may relieve CFS in a wide variety of pathologies. Research may reveal better approaches to safely and conveniently controlling surgical stress and CFS via a modification of the Stress Mechanism at several levels. Medications and treatments might be variously directed at the hypothalamus, SNS, vascular endothelium, thrombin, insoluble fibrin, plasminogen at Factors VII, VIII and XIII.

New anesthesia monitoring devices might be developed that could offer ways to detect activation of the Stress Mechanism and rapidly evaluate the success of stress control measures and treatments. Perhaps pulse oximeter technology could be modified to detect elevations in the blood levels of insoluble fibrin. EKG machines could be merged with ANSAR technology and non-invasive computerized cardiac output technologies to provide continuous appraisal of stress-related effects. Non-invasive techniques to monitor oxygen saturation in the tissue, as a reflection of capillary perfusion, might be possible. Adapting oscillometric blood pressure technology to monitor variations in blood turbulence, as a reflection of blood levels of insoluble thrombin, may offer yet another possibility. As contemplated by the present invention, better clinical strategies for controlling the Stress Mechanism, during and after surgery, may be sought.

Improved understanding of blood viscosity and rheology might offer better guides to red cell and platelet transfusion, in accordance with the present invention. New intravenous fluid preparations might be devised that would better maintain physiologic blood viscosity, coagulability and rheology as well as produce improved vasomotor stability in the present invention the results using presently available colloids and crystalloids. Cardiac bypass pump technology can be modified to impart physiologic levels of turbulence and mixing into the infuscate, thereby mitigating "pump head syndrome" and coagulability problems associated with bypass surgery, in accordance with the present invention. Similar considerations might apply to the design of artificial heart and ventricular assist devices, as encompassed by the present invention.

The problems associated with blood transfusion encompassed by the present invention and over-utilization of crystalloids and colloids is reduceable by the availability of such an intravenous fluid, as per the present invention. Unexpected benefits may accrue from improved maintenance of normal levels of blood viscosity and rheology in the present invention, such as reduction in the incidence of PONV, the cause of which remains poorly understood in the related art.

The present invention uses Stress Theory in its new techniques and medications for minimizing spinal cord damage in the presence of acute injury, speed wound healing, reduce infection, and enable tissue repairs that are presently unimaginable. These techniques and medications in the related art may lead to better techniques for athletic conditioning and performance. They also offer practical ways to extend longevity via better prevention and treatment of atherosclerosis as well as amyloidosis. These aspects of the present invention represent only a few of the possibilities using Stress Theory.

For example, Antinociception Anesthesia method of general anesthesia improves surgical outcome, by controlling and reducing psychic and somatic surgical stress simultaneously, and is preferably employed continuously before, during and after invasive surgical procedures to prevent surgical stress syndrome, in accordance with the present invention. Antinociception Anesthesia may additionally be employed in the treatment of malignancies and atherosclerosis. Antinociception Anesthesia is based upon preventing pathological elevations in Factor VIII blood levels that increase blood viscosity and decrease capillary bed perfusion, i.e., capillary fibrin stress, which cause surgical stress syndrome. Antinociception Anesthesia preferably comprises at least one step and may comprise multiple steps controlling psychic stress, controlling somatic stress, avoiding hypocarbia, avoiding hypoxemia, avoiding hypovolemia, avoiding hypervolemia, and other forms of non-surgical stressful stimuli, inducing mild hypercarbia, and maintaining normal body temperatures at all times.

For example, psychic stress may be controlled by using Sevoflurance or equivalent anesthetic inhalation agents or intravenous hypnotic drugs. Where Sevoflurance is used, it is preferably used in about 0.5 MAC concentrations.

Somatic stress may be controlled by using Fentanyl, which is preferably administered intravenously and may be administered in a loading dose of from about 2 microgram/kg to about 10 microgram/kg before surgical incision. Alternately, an equivalent dosage with other opioid medications such as sufentanil may be used. Treatment of somatic stress may be supplemented by employing additional doses of opioid to prevent SNS activation and/or the respiratory rate may be maintained between about 8 breaths/min to about 12 breaths/minute before emergence. Somatic stress may also be controlled using intravenous infusions of lidocaine as an alternative to, or as a supplement to, treatment with opioids. For example, an intravenous infusion of lidocaine at about 0.05 mg/kg/hr to about 1 mg/kg/hr may be used to prevent somatic stress.

Mild hypercarbia may be induced by endotracheal intubation and the use of controlled ventilation, preferably with continuous monitoring. Mild hypercarbia is preferably set at about 50 torr to support respiratory drive in the presence of opioid dosage and to encourage cardiac output and tissue perfusion. Also, mask induction is preferably employed for increased safety and to eliminate the need for intravenous hypnotic agents that may prolong emergence. The above-referenced techniques to reduce activation of the Stress Syndrome may also be employed to treat malignant tumors, metastatic malignancies, and systemic inflammatory states.

Malignant tumors, metastatic malignancies and systemic inflammatory conditions may be treated by techniques and medications that inhibit the Stress Mechanism via different pathways so as to synergistically reduce the production and/or function of thrombin. The reduction in thrombin may occur systemically and/or locally. Methods to reduce thrombin in the treatment of tumors, metastatic malignancies and systemic inflammatory conditions include induction and maintenance of Antinociception Anesthesia, as described herein throughout the present treatment process to control psychic and somatic stress as well as Factor VIII levels. Additionally, medications that reduce the activity levels of Factor VII may be employed as a supplement or as an alternative.

By way of example only, Factor VII inhibitors, such as low molecular weight heparin or tinzaparin (LMWH); unfractionated heparin (UFH), TFPI (tissue factor pathway inhibitor) synthesized by the vascular endothelium; anti-Factor VIIa and other blockers of Factor VIIa, Xa-TFPI complex, Reviparin, nematode/hookworm anticoagulant protein (rNAPc2), recombinant tissue factor pathway inhibitor, monoclonal anti-TF antibody (AP-1), PHA-798, enoxaparin, dalteparin, pyrazinone TF/VIIa inhibitor, available from Pfizer (compound 34) and low doses of warfarin may be used alone or in combination with other coagulation inhibitors to decrease the above-noted effects of the Stress Syndrome.

To decrease the effects of the Stress Syndrome and to aid in treating conditions such as, atherosclerosis, malignant tumors, metastatic malignancies and systemic inflammatory states, a suitable dosage of tinzaparin, e.g. about 75 U/kg qd to about 175 U/kg qd for enoxaparin, a suitable dosage may be about 1 mg/kg bid. For dalterparin, a suitable dosage may be about 120 U/Kg bid and a suitable dosage of Raviparin may be about 10 mg/kg or about 30 to about 50 IU/kg Q about 12 hours may be administered. A suitable dosage of UFH for the treatments described herein may be determined on the basis of activated partial thromboplastin time (APTT), i.e., twice the normal or whole-blood clotting time or thrice the control value. A suitable dosage of rNAPc2 may be about 3 mg/kg. A suitable dosage of PHA-798 may be from about 100 to about 200 mg/kg/min.

Coagulation inhibitors may also be used mg/kg/min in combination with apoptosis to treat malignancy. For example, coagulation inhibitors in combination with chemotherapy agents such as camptothecin and fas ligand may be used.

Techniques and medications that inhibit the Stress Mechanism and/or reduce the production and/or function of thrombin, including for the treatment of tumors, metastatic malignancies, atherosclerosis and systemic inflammatory conditions, may additionally include the administration of medications that reduce the activity levels of thrombin, Factor X and Factor Xa and techniques that avoid hypothermia, hypocarbia, hypoxia, hyperoxia, and other stressful stimuli that may activate the Stress Syndrome. For example, recombinant tick anti-coagulant protein (rTAP); tinzaparin, Fondaparinux and rNAPc2, Indraparinux, and Parnaparin may be used to reduce the levels of Factor X and Factor Xa. A suitable dosage of rTAP may be about 1 mg/kg bolus followed by 3 mg/kg per hour. A suitable dosage of tinzaparin may be about 175 IU/kg. A suitable dosage of Fondaparinux may be from about 2.2 to about 10 QD. A suitable dosage of rNAPc2 may be from about 0.3 mg/kg to about 5 mg/kg; and a suitable dosage of Parnaparin may be about 100 IU/kg.

Suitable thrombin inhibitors may include, for example, warfarin (coumadin), annexin V, Ximelagatran, Melagatran, hirudin, bivalirudin, and argatroban. A suitable dosage of Ximelagatran may be from about 24 mg bid to about 36 mg bid orally. Melagatran may be administered intravenously or subcutaneously. A suitable dosage of warfarin may be from about INR 2.0 to about INR 3.0. A suitable dosage of Hirudin may be from about 0.006 to about 0.24 mg/kg/hour IV infusion. A suitable dosage of bivalirudin may be about 0.75 mg/kg bolus and about 1.75 mg/kg hour infusion. A suitable dosage of argatroban may be from about 0.5 to about 2 mµg/kg/minute. Suitable inhibitors of Factor VIII may include, for example, local anesthetic infusions, opioids, sedative-hypnotic agents, and inhalation agents, and combinations thereof.

The above-referenced compounds and medications that inhibit the Stress Mechanism and Factor VIII, Factor VII, Factor X, Factor Xa and thrombin may be delivered by employing a skin patch or skin peel. For example, the above-referenced medications may be delivered via a skin patch or skin peel to induce localized apoptosis to treat skin malignancies and other abnormal skin lesions. Suitable skin patch and skin peel technologies may include materials marketed by Zars, Inc. of Salt Lake City, Utah.

Avoiding hypothermia, hypocarbia, hypoxia, hyperoxia, and other stressful stimuli that may cause activation of the Stress Mechanism may also be used alone, or in combination with the methods and compositions disclosed herein, to reduce the Stress Mechanism and to treat atherosclerosis, improve surgical outcome, treat tumors, metastatic malignancies, and systemic inflammatory conditions. For example, use of tube feeding techniques to the distal ileum may be employed to prevent activation of the Stress Syndrome due to starvation during the treatment process. Careful padding may be used to protect the patient's body from trauma that may create a hemorrhage in the presence of suppression of blood coagulation. Use of special beds to regularly change the patient's body position minimizes the risk of pressure injury. The patient emerges from anesthesia after completion of treatment and restoration of safe blood coagulability levels.

Atherosclerosis may be treated and reversed by decreasing the Stress Mechanism via medications and techniques and/or via increasing blood turbulence and mixing in the present invention. For example, ultrasound techniques may be used to increase blood turbulence and mixing in the present invention. Ultrasound may be induced in the blood via external ultrasound devices and/or induced by pulsed laser radiation. The pulsed laser radiation may be delivered via an intra-arterial fiberoptic catheter. Ultrasound is generated externally and delivered to the intra-arterial treatment location via an intra-arterial catheter or is generated at the tip of an intra-arterial catheter by a miniaturized ultrasound generator device.

Blood viscosity may also be decreased by reducing blood levels of red cell mass, by reducing blood levels of fibrin and fibrinogen by plasmapheresis or medications, or by combinations thereof in the present invention. An intravenous blood substitute solution preferably comprises fibrinogen, albumen, and electrolytes in the present invention. The electrolytes may include sodium, potassium, magnesium and trace elements found in normal blood. The fibrinogen may comprise human fibrinogen, animal fibrinogen, and combinations thereof. The blood substitute may be used for rapidly restoring normal blood viscosity, rheology, osmolarity, turbulence, and mixing and hemodynamic stability.

While the present invention has been described with regards to particular embodiments, it is recognized that additional variations of the present invention may be devised without departing from the inventive concept.

INDUSTRIAL APPLICABILITY

The present invention industrially applies to methods useful in treating surgical stress syndrome, circulatory disorders, malignancies and for providing a blood substitute in an organism. The methods and treatments disclosed herein industrially applies to methods and compositions that stabilize the turbulence of an organism's blood in order to treat stress-related disease.

What is claimed:
1. A method of decreasing Factor VIII elevation in blood by controlling psychic and somatic surgical stress, said method comprising the steps of:
   a. controlling the psychic stress in the organism by administering to the organism at least one compound selected from the group consisting of a Sevoflurance, an anesthetic inhalation agent, and an intravenous hypnotic drug;
   b. controlling the somatic stress by administering to the organism at least one compound selected from the group consisting of an opioid and lidocaine;
   c. maintaining a normal body temperature of the organism;
   d. minimizing a non-surgical stress stimuli; and
   e. allowing a mild hypercarbia to support a respiratory drive in the presence of an opioid dosage to offset a respiratory effect of the opioid and encourage cardiac output, wherein elevation of Factor VIII is decreased.

2. The method of claim 1, wherein the concentration of Sevoflurance is about 0.5 minimum alveolar concentration ("MAC").

3. The method of claim 1, wherein, the opioid comprises a compound selected from the group consisting of a Fentanyl and a sufentanil.

4. The method of claim 3, wherein Fentanyl is administered intravenously in a dose of about two micrograms/Kg to about ten micrograms/Kg before surgical incision.

5. The method of claim 1, further comprising the step of giving additional doses of an opioid as necessary to prevent sympathetic nervous system activation.

6. The method of claim 1, further comprising the step of giving additional doses of an opioid to maintain a respiratory rate of about 8 breaths per minute to about 12 breaths per minute before emergence.

7. The method of claim 1, wherein the lidocaine is infused intravenously to the organism in a dosage of approximately 0.05 mg/Kg per hour to approximately 1.0 mg/Kg per hour.

8. The method of claim 1, wherein the non-surgical stressful stimulus is selected from the group consisting of a hypothermia, a hypocarbia, a hypoxemia, a hyperoxia, a hypovolemia and a hypervolemia.

9. The method of claim 1, wherein an endotracheal intubation and a controlled ventilation are used to cause a mild hypercarbia.

10. The method of claim 9, wherein the mild hypercarbia is approximately 50 torr.

11. The method of claim 3, wherein sufentanil is administered intravenously in a dose of about two micrograms/Kg to about ten micrograms/Kg before surgical incision.

* * * * *